(12) United States Patent
Naccari et al.

(10) Patent No.: US 8,138,357 B2
(45) Date of Patent: Mar. 20, 2012

(54) COMPOUNDS AND THEIR SALTS SPECIFIC TO THE PPAR RECEPTORS AND THE EGF RECEPTORS AND THEIR USE IN THE MEDICAL FIELD

(75) Inventors: Giancarlo Naccari, Monza (IT); Sergio Baroni, Villa d'Adda (IT)

(73) Assignee: Giuliani International Limited, Dublin (IE)

( * ) Notice: Subject to any disclaimer, the term of this patent is extended or adjusted under 35 U.S.C. 154(b) by 835 days.

(21) Appl. No.: 11/989,033

(22) PCT Filed: Jul. 24, 2006

(86) PCT No.: PCT/IE2006/000076
§ 371 (c)(1),
(2), (4) Date: Jun. 6, 2008

(87) PCT Pub. No.: WO2007/010514
PCT Pub. Date: Jan. 25, 2007

(65) Prior Publication Data
US 2009/0118357 A1    May 7, 2009

(30) Foreign Application Priority Data
Jul. 22, 2005  (IT) .............................. RM2005A0390

(51) Int. Cl.
C07D 311/02   (2006.01)
C07D 211/08   (2006.01)
A61K 31/44    (2006.01)

(52) U.S. Cl. .......... 549/285; 549/439; 546/16; 514/299; 514/311; 514/314; 514/319; 514/478

(58) Field of Classification Search ................. 549/285, 549/439; 546/192, 168, 16; 562/405, 432; 564/163, 165; 514/299, 311, 314, 319, 478, 514/576, 619
See application file for complete search history.

(56) References Cited

U.S. PATENT DOCUMENTS
3,211,610 A   10/1965 Rogers
(Continued)

FOREIGN PATENT DOCUMENTS
EP   0 055 689 A1   7/1982
(Continued)

OTHER PUBLICATIONS

Date of Mailing Feb. 1, 2007, International Search Report, PCT/IE2006/000076.
(Continued)

*Primary Examiner* — Andrew D Kosar
*Assistant Examiner* — Raymond Covington
(74) *Attorney, Agent, or Firm* — Goodwin Procter LLP

(57) ABSTRACT

Therefore the present invention relates specifically to the compounds of general formula (I), in which $R_1$ and $R_2$, which may be identical or different, are selected from the group comprising H, $-C_nH_{2n-1}$, a linear or branched alkyl group having from 1 to 6 carbon atoms, or together form an aromatic or aliphatic ring with 5 or 6 atoms; $R_3$ is selected from $-CO-CH_3$, $-NHOH$, $-OH$, $-OR_6$ in which $R_6$ is a linear or branched alkyl group having from 1 to 6 carbon atoms; $R_4$ is selected from H, a linear or branched alkyl group having from 1 to 6 carbon atoms, phenyl, benzyl, $-CF_3$ or $-CF_2CF_3$, vinyl or allyl; $R_5$, $R_7$, $R_8$ are hydrogen atoms; or $R_3$ and $R_4$, $R_4$ and $R_5$, or $R_7$ and $R_8$ together form a ring, fused to the benzene, aromatic or aliphatic ring with 5 or 6 atoms comprising from 1 to 2 heteroatoms selected independently from the group comprising N, O. and use thereof in the medical field.

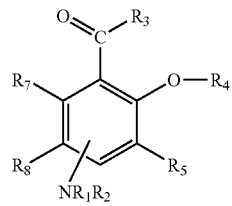

(I)

18 Claims, 15 Drawing Sheets

Increase in expression of PPARγ protein by the epithelial cells induced by compounds 17, 26 and 31;
Western blot evaluation of PPARγ protein expression in untreated cells (control) and cells treated with the novel compounds, 5-ASA (30mM) or Rosiglitazone;
Calculated optical density values of the PPARγ using β-actin as internal control

U.S. PATENT DOCUMENTS

| | | | |
|---|---|---|---|
| 3,444,232 | A | 5/1969 | Bernstein |
| 4,036,951 | A | 7/1977 | Halpern et al. |
| 4,429,152 | A | 1/1984 | Gries et al. |
| 4,933,330 | A | 6/1990 | Jorgensen et al. |
| 5,262,549 | A | 11/1993 | Telfer et al. |
| 5,302,751 | A | 4/1994 | Manimaran et al. |
| 5,519,014 | A | 5/1996 | Borody |
| 5,594,151 | A | 1/1997 | Stolowitz |
| 6,194,627 | B1 | 2/2001 | Geissler et al. |
| 6,326,364 | B1 | 12/2001 | Lin et al. |
| 6,583,128 | B2 | 6/2003 | Ekwuribe et al. |
| 7,098,025 | B1 | 8/2006 | Auwerx et al. |
| 7,429,676 | B2 | 9/2008 | Woltering et al. |
| 2003/0113815 | A1 | 6/2003 | Houseknecht et al. |
| 2003/0133875 | A1 | 7/2003 | Kelly |
| 2003/0220374 | A1 | 11/2003 | Needleman |
| 2003/0229083 | A1 | 12/2003 | Debnath et al. |
| 2004/0034067 | A1 | 2/2004 | MacPhee |
| 2004/0115127 | A1 | 6/2004 | Wright et al. |
| 2004/0132110 | A1 | 7/2004 | Desreumaux et al. |
| 2006/0177444 | A1 | 8/2006 | Horizoe |
| 2006/0270635 | A1 | 11/2006 | Wallace et al. |
| 2009/0048343 | A1 | 2/2009 | Naccari et al. |
| 2011/0105748 | A1 | 5/2011 | Bhuniya et al. |

FOREIGN PATENT DOCUMENTS

| | | |
|---|---|---|
| EP | 0102833 A1 | 3/1984 |
| EP | 0291159 A2 | 11/1988 |
| EP | 0352826 A2 | 1/1990 |
| EP | 1 285 908 A1 | 2/2003 |
| EP | 1348698 A1 | 10/2003 |
| GB | 767788 A | 2/1957 |
| WO | WO-94/00135 A1 | 1/1994 |
| WO | WO-95/31194 A1 | 11/1995 |
| WO | WO-98/06387 A2 | 2/1998 |
| WO | WO-98/43081 | 10/1998 |
| WO | WO-00/59866 A1 | 10/2000 |
| WO | WO-01/02388 A1 | 1/2001 |
| WO | WO-01/79153 A1 | 10/2001 |
| WO | WO-02/095393 A2 | 11/2002 |
| WO | WO-2004/073622 A2 | 9/2004 |
| WO | WO 2005/012280 A1 | 2/2005 |
| WO | WO-2005/072113 A2 | 8/2005 |
| WO | WO-2005/084658 A1 | 9/2005 |
| WO | WO-2006/072175 A1 | 7/2006 |
| WO | WO-2007/010514 A2 | 1/2007 |
| WO | WO 2007/010516 A2 | 1/2007 |
| WO | WO-2007/010516 A2 | 1/2007 |
| WO | WO-2008/104557 A1 | 9/2008 |
| WO | WO-2009/080828 A2 | 7/2009 |
| WO | WO-2010/063470 A2 | 6/2010 |
| WO | WO-2010/063472 A1 | 6/2010 |
| WO | WO-2010/091892 A2 | 8/2010 |
| WO | WO-2010/091894 A2 | 8/2010 |

OTHER PUBLICATIONS

Date of Mailing Feb. 1, 2007, Written Opinion of the International Searching Authority, PCT/IE2006/000076.

Date of Mailing Jan. 22, 2008, International Preliminary Report on Patentability, PCT/IE2006/000076.

Ahnfelt-Ronne, Ian, et al. (1990) "Clinical Evidence Supporting the Radical Scavenger Mechanism of 5-Aminosalicylic Acid," Gastroenterology, 98: 1162-1169.

Allgayer, H. (2003) "Review Article: Mechanisms of Action of Mesalazine in Preventing Colorectal Carcinoma in Inflammatory Bowel Disease," Aliment Pharmacol. Ther., 18 (Suppl. 2): 10-14.

Liao, Yun-Zhang, et al. (1990) "Therapeutic Effect of Methyl 5-Aminosalicylate on Experimental Ulcerative Colitis in Rabbits," Acta Pharmacologica Sinica, 11(1): 54-56.

Peyrin-Biroulet, L., et al. (2007) "Peroxisome Proliferator-Activated Receptor Gamma Functions as an Antibacterial Factor," Journal of Crohn's and Colitis Supplements, 1(1).

Reifen, Ram, et al. (2004) "5-ASA and Lycopene Decrease the Oxidative Stress and Inflammation Induced by Iron in Rats with Colitis," J. Gastroenterol, 39: 514-519.

Schauber, Jurgen, et al. (2004) "Histone-Deacetylase Inhibitors Induce the Cathelicidin LL-37 in Gastrointentinal Cells," Molecular Immunology, 41(9): 847-854.

Schwab, Markus, et al. (2007) "Role of Nuclear Hormone Receptors in Butyrate-Mediated Up-Regulation of the Antimicrobial Peptide Cathelicidin in Epithelial Colorectal Cells," Molecular Immunology, 44(8): 2107-2114.

van't Riet, Bart, et al. (1979) "Synthesis of Hydroxy and Amino-Substituted Benzohydroxamic Acids: Inhibition of Ribonucleotide Reductase and Antitumor Activity," Journal of Medicinal Chemistry, 22(5): 589-592.

Wang, Tian-Tian, et al. (2004) "Cutting Edge: 1,25-Dihydroxyvitamin D3 is a Direct Inducer of Antimicrobial Peptide Gene Expression," The Journal of Immunology, 173: 2909-2912.

Williams, J.G., et al. (1989) "Effect of Sulphasalazine and its Active Metabolite, 5-Amino-Salicylic Acid, on Toxic Oxyden Metabolite Production by Neutrophils," Gut, 30: 1581-1587.

Beilstein Database, Beistein Institut zur Förderung der Chemischen Wissenschaften, Frankfurt an Main, DE, XP002413836, Accession No. 1869425, J Labelled Compd Radiopharm, 44: S225-S227 (2001).

Beilstein Database, Beistein Institut zur Förderung der Chemischen Wissenschaften, Frankfurt an Main, DE, XP002413837, Accession No. 2367395, Chem Ber, 87: 179-181 (1954).

Beilstein Database, Beistein Institut zur Förderung der Chemischen Wissenschaften, Frankfurt an Main, DE, XP002413838, Accession No. 2839685, J Am Chem Soc, 73: 903-904 (1951).

Beilstein Database, Beistein Institut zur Förderung der Chemischen Wissenschaften, Frankfurt an Main, DE, XP002413839, Accession No. 2092096, J Med Chem, 22: 589 (1979).

Beilstein Database, Beistein Institut zur Förderung der Chemischen Wissenschaften, Frankfurt an Main, DE, XP002413840, Accession No. 3031462, Bull Soc Chim Belg, 61: 310-320 (1952).

Beilstein Database, Beistein Institut zur Förderung der Chemischen Wissenschaften, Frankfurt an Main, DE, XP002413841, Accession No. 2641495, J Org Chem, 27: 3283-3295 (1962).

Beilstein Database, Beistein Institut zur Förderung der Chemischen Wissenschaften, Frankfurt an Main, DE, XP002413842, Accession No. 3259704, Justus Liebigs Ann Chem, 429: 173 (1922).

Beilstein Database, Beistein Institut zur Förderung der Chemischen Wissenschaften, Frankfurt an Main, DE, XP002413843, Accession No. 3530419, Justus Liebigs Ann Chem, 429: 164 (1922).

Allgayer, H., "Review Article: Mechanisms of Action of Mesalazine in Preventing Colorectal Carcinoma in Inflammatory Bowel Disease," Aliment Pharmacol. Ther. 18(2):10-14 (2003).

Rousseaux, C., et al., "Intestinal Antiinflammatory Effect of 5-Aminosalicylic Acid is Dependent on Peroxisome Proliferator-Activated Receptor-γ," JEM 201(8): 1205-1215 (2005).

Bull, A.W., "The Role of Peroxisome Proliferator-Activated Receptor γ in Colon Cancer and Inflammatory Bowel Disease," Arch Pathol Lab Med, 127: 1121-1123 (2003).

Koeffler, H.P., "Peroxisome Proliferator-activated Receptor γ and Cancers," Clinical Cancer Research, 9: 1-9 (2003).

Youssef, J., et al., "Role of Peroxisome Proliferator-Activated Receptors in Inflammation Control," J Biomed Biotechnol., 3: 156-166 (2004).

Dubuquoy, L., et al., "Role of peroxisome proliferator-activated receptor γ and retinoid X receptor heterodimer in hepatogastroenterological diseases," The Lancet, 360:1410-1418 (2002).

Osawa, E., et al., "Peroxisome Proliferator-Activated Receptor γ Ligands Suppress Colon Carcinogenesis Induced by Azoxymethane in Mice," Gastroenterology, 124: 361-367 (2003).

Tanaka, T., et al., "Ligands for Peroxisome Proliferator-activated Receptors α and γ Inhibit Chemically Induced Colitis and Formation of Aberrant Crypt Foci in Rats," Cancer Res, 61: 2424-2428 (2001).

Mendelsohn, J., "The epidermal growth factor receptor as a target for cancer therapy," Endocr Relat Cancer, 8: 3-9 (2001).

Harari, P.M., "Epidermal growth factor receptor inhibition strategies in oncology," Endocr Relat Cancer, 11: 689-708 (2004).

Brunton, V.G., et al., "A role for epidermal growth factor receptor, c-Src and focal adhesion kinase in an in vitro model for the progression of colon cancer," Oncogene, 14: 283-293 (1997).

Kari, C., et al., "Targeting the Epidermal Growth Factor Receptor in Cancer: Apoptosis Takes Center Stage," *Cancer Res*, 63: 1-5 (2003).

Dubuquoy, L., et al.,"Impaired Expression of Peroxisome Proliferator-Activated Receptor gamma in Ulcerative Colitis," *Gastroenterology*, 124: 1265-1276 (2003).

Clark, M., et al., "Validation of the General Purpose Tripos 5.2 Field," *J Comput Chem.*, 10: 982-1012 (1989).

Gampe, R.T., Jr., et al., "Asymmetry in the PPARγ/RXRα Crystal Structure Reveals the Molecular Basis of Heterodimerization among Nuclear Receptors," *Mol Cell*, 5: 545-555 (Mar. 2000).

Jones, G., et al., "Development and validation of a genetic algorithm for flexible docking," *J Mol. Biol.*, 267: 727-748 (1997).

Wang, R., et al., "Further development and validation of empirical scoring functions for structure-based binding affinity prediction," *J Comput Aided Mol Des*, 16: 11-26 (2002).

Westin, S., et al., "Interactions controlling the assembly of nuclear-receptor heterodimers and co-activators," *Nature*, 395: 199-202 (Sep. 1998).

Mangelsdorf, D.J., et al., "The nuclear receptor superfamily: the second decade," *Cell*, 83: 835-839 (Dec. 1995).

Misra, P., et al., "Phosphorylation of transcriptional coactivator peroxisome proliferator-activated receptor (PPAR)-binding protein (PBP). Stimulation of transcriptional regulation by mitogen-activated protein kinase," *J Biol Chem*, 277: 48745-48754 (2002).

Gerdes, J., et al. "Growth fractions in breast cancers determined in situ with monoclonal antibody Ki-67," *J Clin Pathol*, 39: 977-80 (1986).

Nolte, R.T., et al., "Ligand binding and co-activator assembly of the peroxisome proliferator-activated receptor-γ," *Nature*, 395: 137-143 (Sep. 1998).

Xu, H.E., et al., "Structural determinants of ligand binding selectivity between the peroxisome proliferator-activated receptors," *Proc Natl Acad Sci U S A*, 98: 13919-13924 (2001).

International Search Report issued on Feb. 1, 2007, in parent PCT Application No. PCT/IE2006/000076, 5 pages.

International Preliminary Report on Patentability, with Written Opinion, issued on Jan. 22, 2008, in parent PCT Application No. PCT/IE2006/000076, 10 pages.

Beilstein Database, Beilstein Institute for Organic Chemistry, Frankfurt an Main, DE, retrieved from XFIRE, ,Accession No. brn 3200601, *J. Chem. Soc.*, p. 104, 111 (1935).

Beilstein Database, Beilstein Institute for Organic Chemistry, Frankfurt an Main, DE, retrieved from XFIRE, , Accession No. brn 3242057, *Chem. Ber.*, 74: 500,517 (1941).

Beilstein Database, Beilstein Institute for Organic Chemistry, Frankfurt an Main, DE, retrieved from XFIRE, , Accession No. brn 3199917, *Chem. Ber.*, 46: 288 (1913).

Beilstein Database, Beilstein Institute for Organic Chemistry, Frankfurt an Main, DE, retrieved from XFIRE, , Accession No. brn 3199913, *Chem. Ber.*, 46: 3978 (1913).

Beilstein Database, Beilstein Institute for Organic Chemistry, Frankfurt an Main, DE, retrieved from XFIRE, , Accession No. brn 3296969, *Chem. News J. Ind. Sci.*, 36: 269 (1877).

Beilstein Database, Beilstein Institute for Organic Chemistry, Frankfurt an Main, DE, retrieved from XFIRE, , Accession No. pcrn 859019, US Patent No. 4,429,152 A (Jan. 1984).

Beilstein Database, Beilstein Institute for Organic Chemistry, Frankfurt an Main, DE, retrieved from XFIRE, , Accession No. brn 3268495, *Justus Liebigs Ann. Chem.*, 436: 60 (1924).

Beilstein Database, Beilstein Institute for Organic Chemistry, Frankfurt an Main, DE, retrieved from XFIRE, , Accession No. brn 2208094, *J. Am. Chem. Soc.*, 68: 2335, 2338 (1946).

Beilstein Database, Beilstein Institute for Organic Chemistry, Frankfurt an Main, DE, retrieved from XFIRE, , Accession No. brn 2803076, *J. Org. Chem.*, 14: 1013, 1018 (1949).

Baker, B.R., et al., "Potential Anticancer Agents. LXXVIII Nonclassical Antimetabolites. IV. Synthesis of Compounds Related to 4-(Iodoacetamido) Salicylie Acid, an Exo-Alkylating Irreversible Inhibitor," Journal of Organic Chemistry, vol. 27 (1962) p. 3283-3295.

Brown, et al., "Chimie Organique," C.R. Acad. Sc. Paris, t. 287 (1978) 287(4), 125-8.

Database Caplus Chemical Abstracts Service, Columbus, Ohio, US; Database Accession No. 1955: 19868, Abstract of Mann et al.: Chemical & Industry (London, United Kingdom) (1954 373-4.

Database Caplus Chemical Abstracts Service, Columbus, Ohio, US; Database Accession No. 1949: 23214, Abstract of Tomcsik et al.: Helvetica Chimica Acta (1949), 32, 31-4.

Database Caplus Chemical Abstracts Service, Columbus, Ohio, US; Database Accession No. 1913-10241, Abstract of Heller: Berichte der Deutschen Chemischen Gesellschaft (1913), 46, 280-94.

Delbarre, F., et al., "Non-Steroid Antiinflammatory Substances. I. Derivatives of the 4- and 5-Aminosalicylic Acids," Medicina Experimentalis, (1964) 11(5), p. 325-32.

Deljac, A., et al., "Absolute Configuration of (—)-β-Hydroxy-β-(*m*)-Hydroxyphenyl)-Propionic Acid," Recueil 86 (1967), 765-768.

Examination Report dated Apr. 15, 2011 for Application No. 06 766 083.7-2103 (11 pages).

Guo, et al., "Effect of Uyghur Compound Xipayi Kui Jie' an on the Ultrastructure of Small Intestinal Epithelial Cell in Rat Model of Ulcerative Colitis," Journal of Xinjiang Medical University (2009) 32 (7) , p. 893-894.

Husova, Libuse, et al., "Hepatopathy, coeliac disease and lymphocytic colitis," Ceska A. Slovenska Gastroenterologie A. Hepatologie—Czech and Slovak Gastroenterology and Hepatology, 61 (6) (2007), 309-313.

International Search Report for PCT/EP2008/068265, mailed Aug. 11, 2009, 6 pages.

J. Med. Chem. 1985, 28, p. 717-727.

J. Phys. Chem, 1989, 93, p. 5979-5980.

Journal of Chemical and Engineering Data, vol. 14, No. 3, 1969, p. 388-391.

Journal of Labelled Compounds and Radiopharmaceuticals, vol. XXIX, No. 10, 1991, p. 1149-1155.

Mager, Von P.P., et al., "Struktur-Wirkungs-Beziehungen bei Salizylsaure- und Benzoesaurederivaten," Zbl. Pharm. 118 (1979) Heft 12, p. 1259-1275.

Sherwin, C.P., "Acetylation as a Physiologic Reaction," Scientific Proceedings (1924), 22, 182.

Tuleu, et al., "Colonic delivery of 4-aminosalicylic acid using amylose-ethyl cellulose-coated hydroxypropyl methyl cellulose capsules," Aliment Pharmacol Ther., (2002); 167: 1771-1779.

Yanai, K., et al., "Para-Position Derivatives of Fungal Anthelmintic Cyclodepsipeptides Engineered with *Streptomyces venezuelae* Antibiotic Biosynthetic Genes," Nature Biotechnology (2004) 22, 848-855.

Database Chemcats [Online] Chemical Abstracts Service, Columbus, Ohio, Feb. 6, 2008, XP002591674.

International Search Report for PCT/EP2010/000935 mailed on Aug. 23, 2010.

International Search Report for PCT/EP2010/000939 mailed on Sep. 20, 2010.

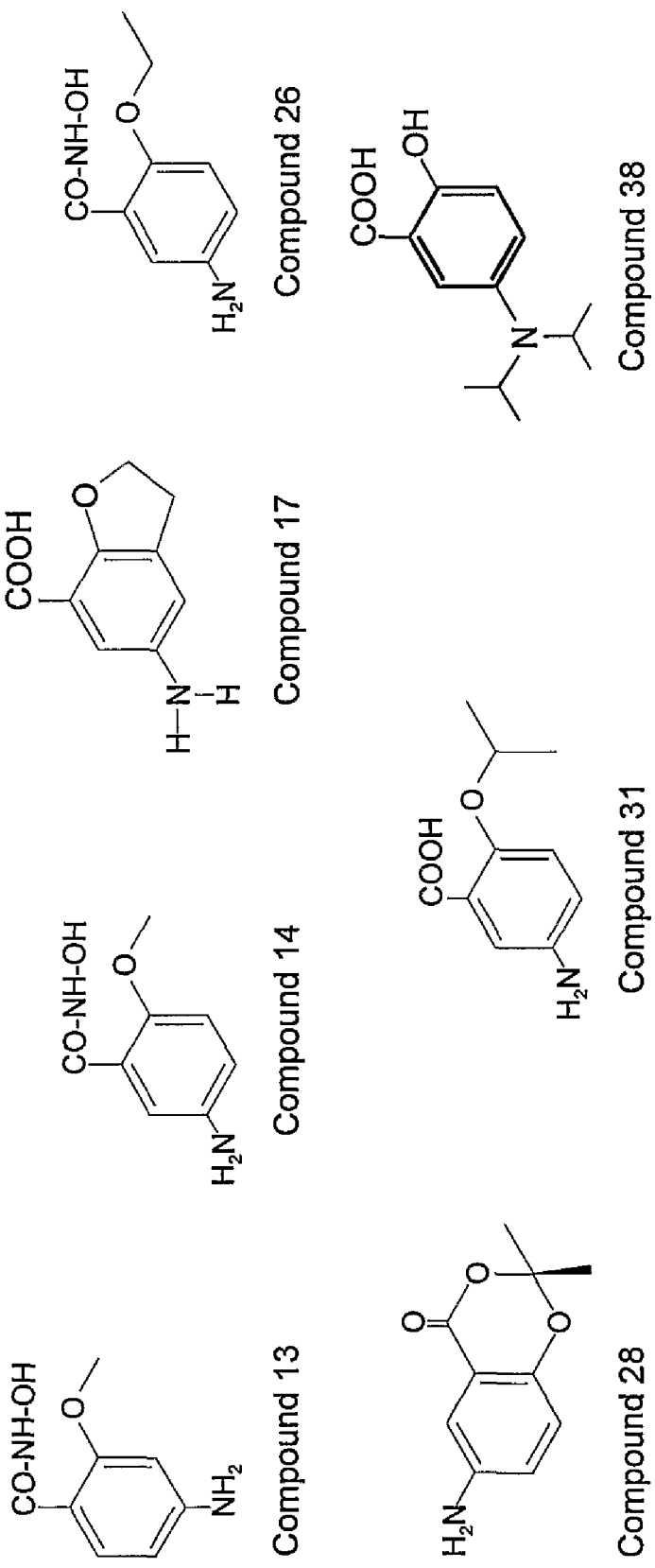
Fig. 1A: Structures of Compounds 13, 14, 17, 26, 31 and 38

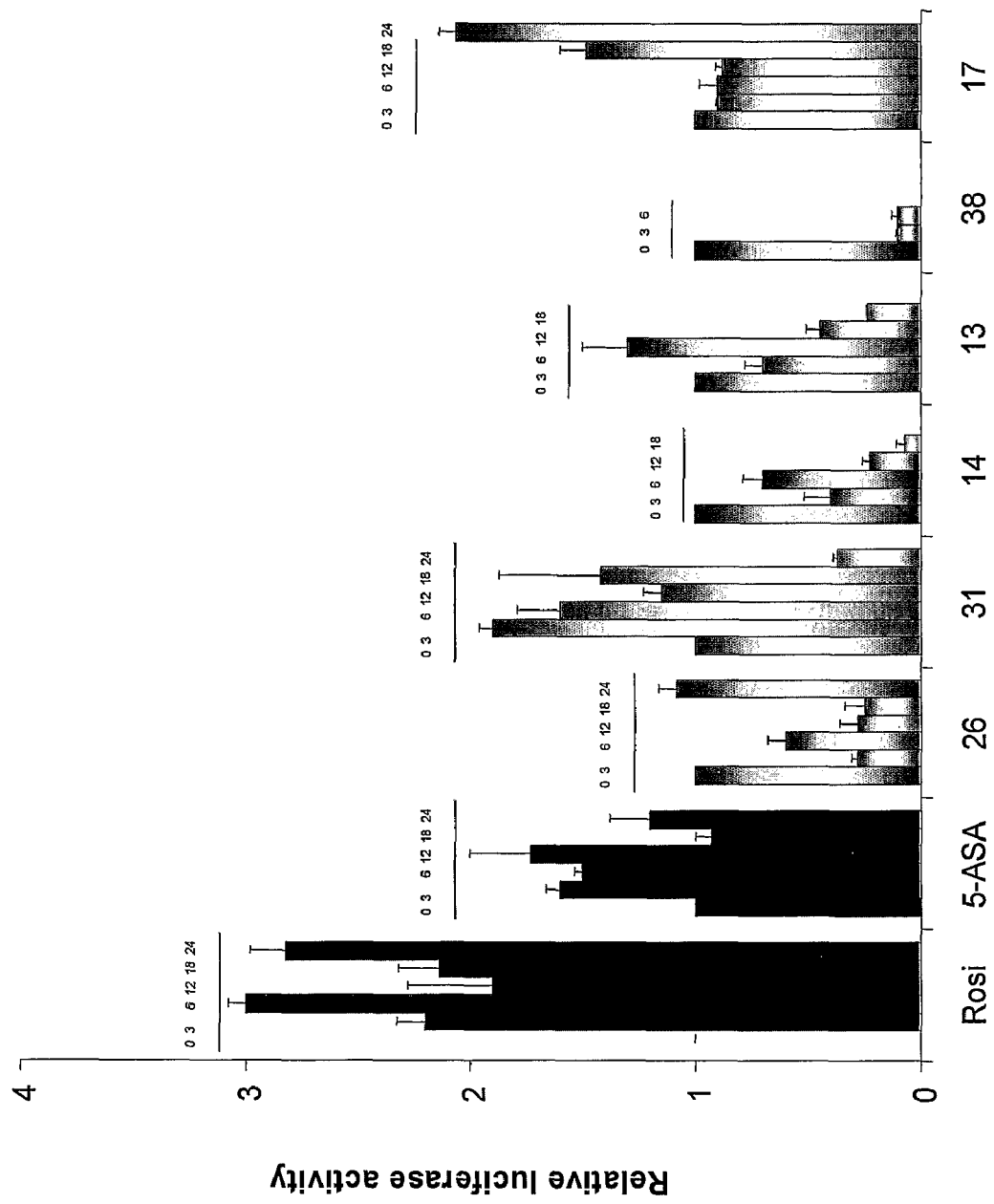
Fig. 1B: Activation of PPARγ Receptors by 17 & 31, in comparison with with 5-ASA and Rosiglitazone Increase in expression of PPARγ protein by the epithelial cells induced by compounds 17, 26 and 31;
Western blot evaluation of PPARγ protein expression in untreated cells (control) and cells treated with the novel compounds, 5-ASA (30mM) or Rosiglitazone;
Calculated optical density values of the PPARγ using β-actin as internal control Fig. 3: Comparison of inhibition of epithelial cells proliferation by 17 and 31 vs. 5-ASA, Rosiglitazone Fig. 4: Induction of apoptosis of epithelial cells by compound 31 vs. 5-ASA, Rosiglitazone

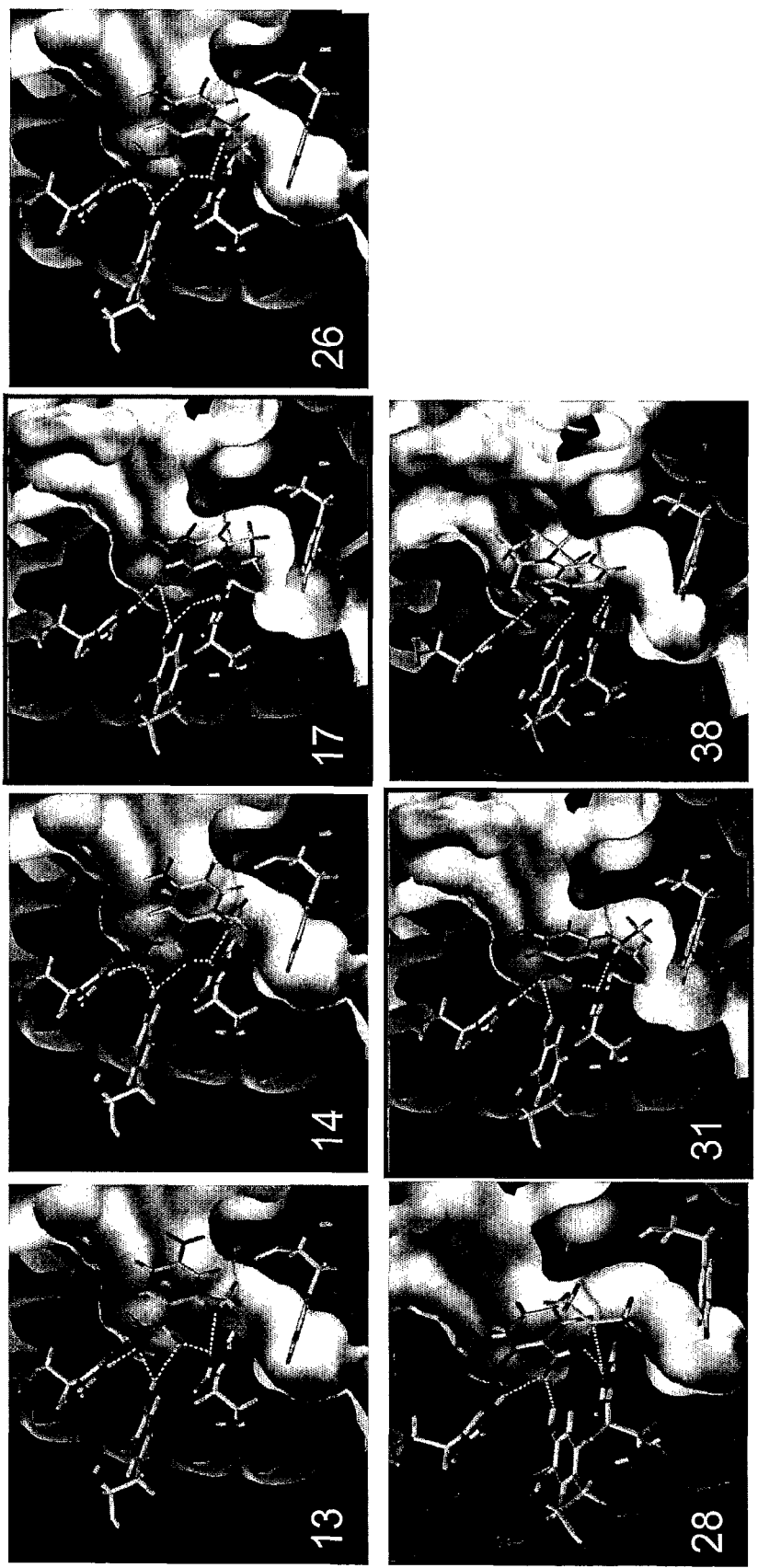
Fig. 5A: Docking analysis of the new molecules (compounds 13, 14, 17, 26, 28, 31, 38) (hydrogen bonding interactions are shown)

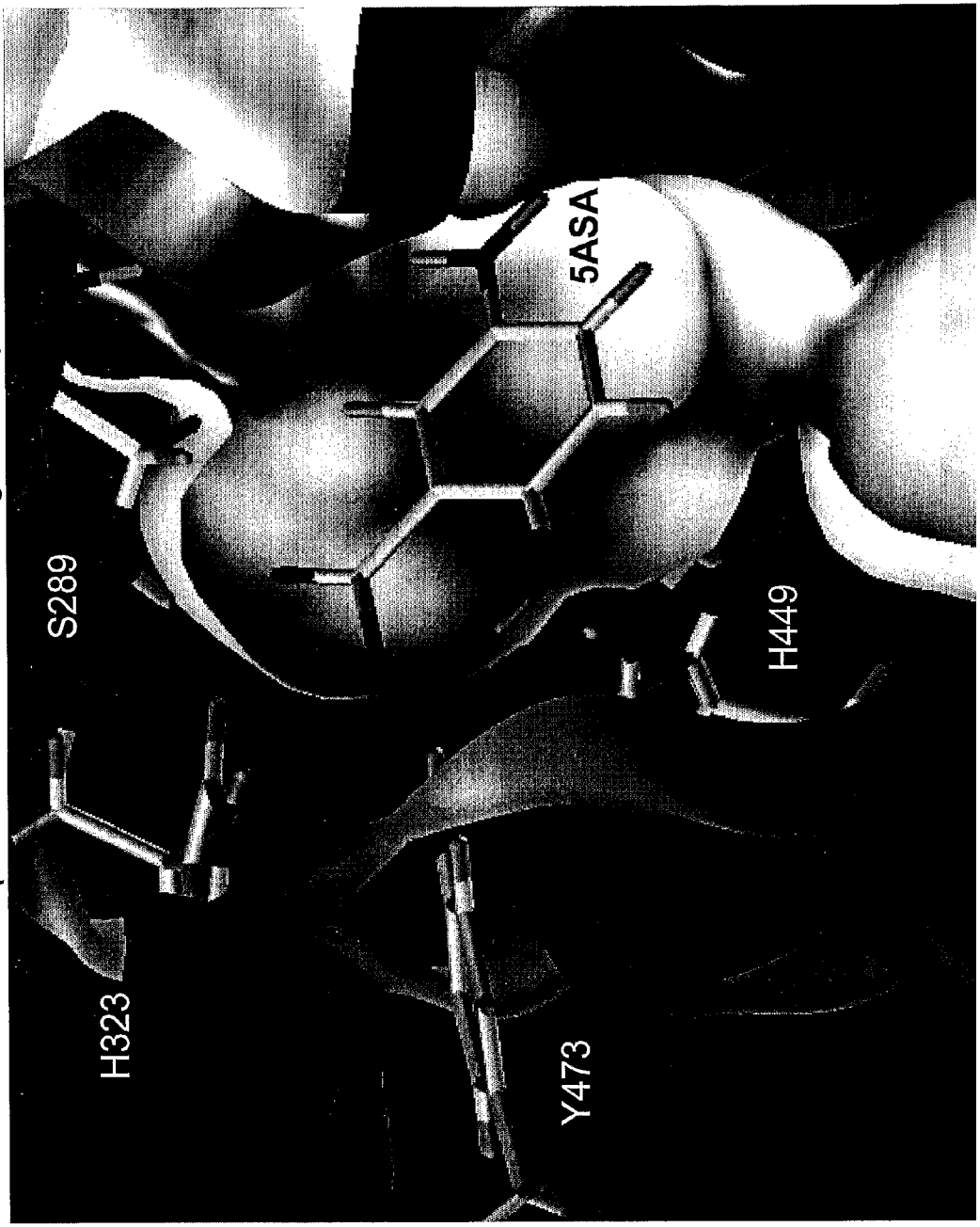
Fig 5B: Docking of 5-aminosalicylic acid (mesalamine) to PPAPγ receptor (amino acid residues labeling is shown)

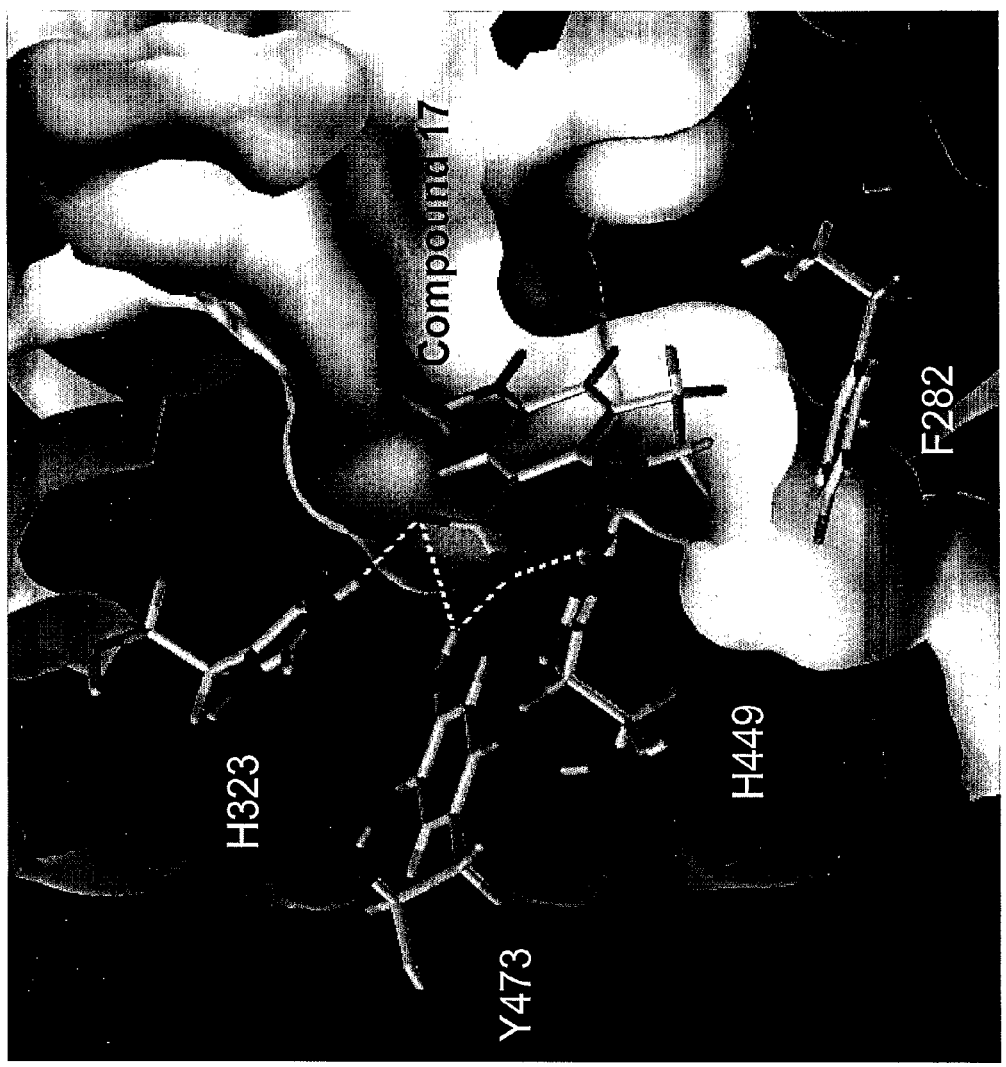
Fig. 5C: More detailed receptor docking of compound 17 (amino acid residues labeling and hydrogen bonding interactions are shown)

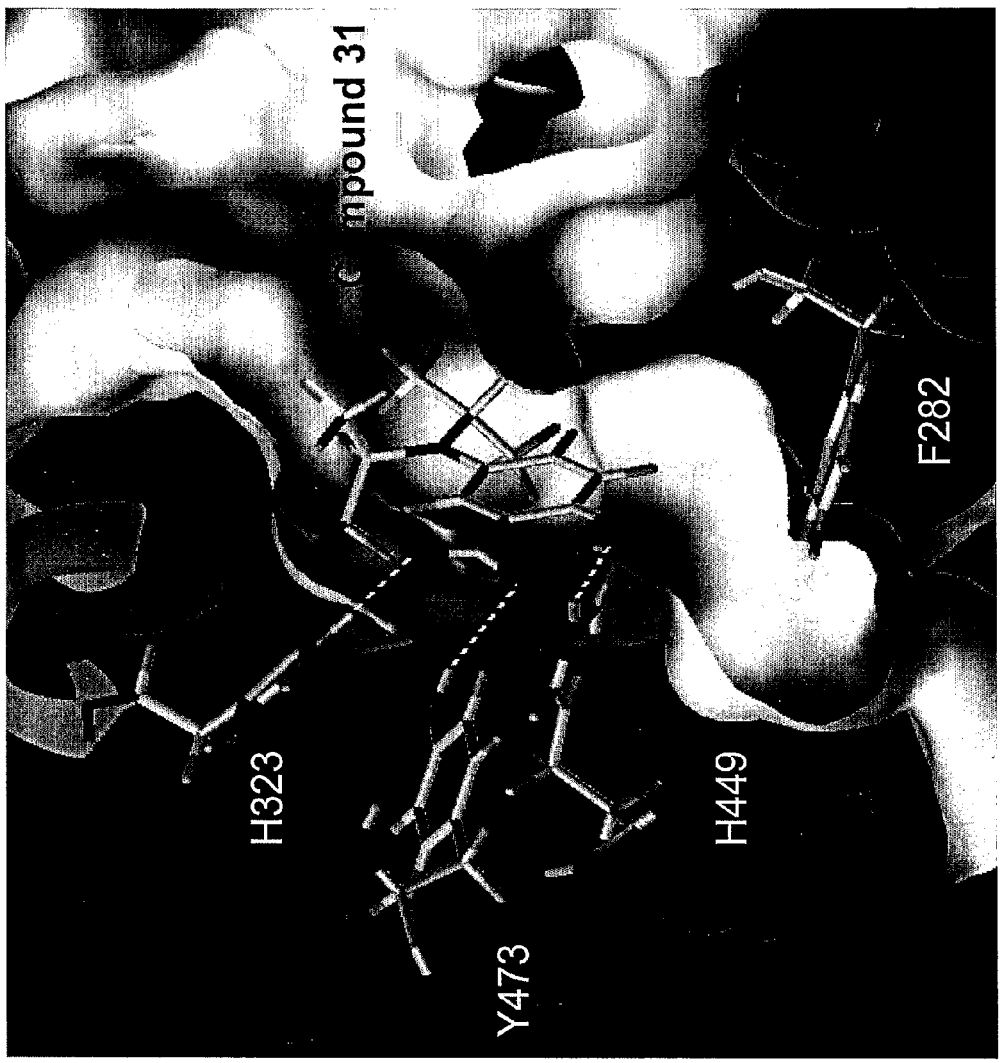
FIG. 5D: More detailed receptor docking of compound 31 (amino acid residues labeling and hydrogen bonding interactions are shown)

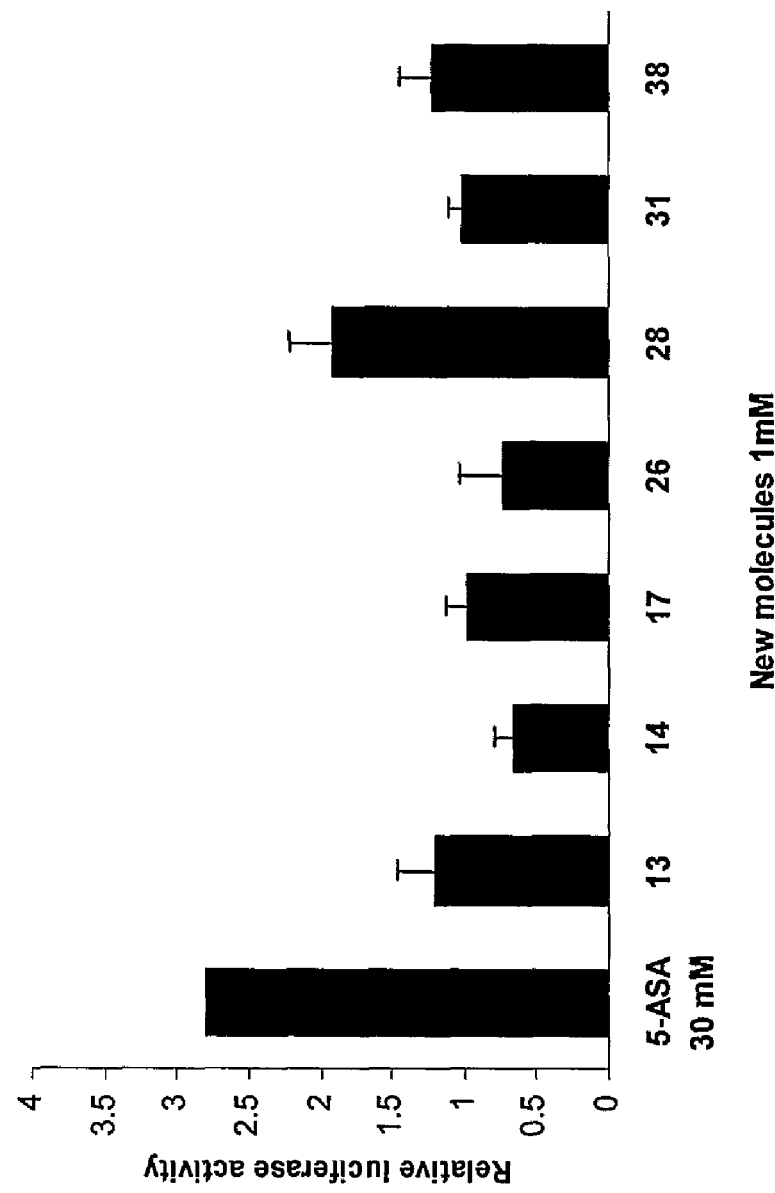
Fig. 6: Analysis of PPARγ activity of compounds 13, 14, 17, 26, 28, 31 and 38, in transfected HT-29 cells at 1mM vs 30 mM 5-ASA Fig. 7: Proliferation of HT29, HT115 and DLD1 human colon carcinoma cell lines on treatment with 0.5-10 mM novel compound 13, 14, 31 and 38, for 48 hours
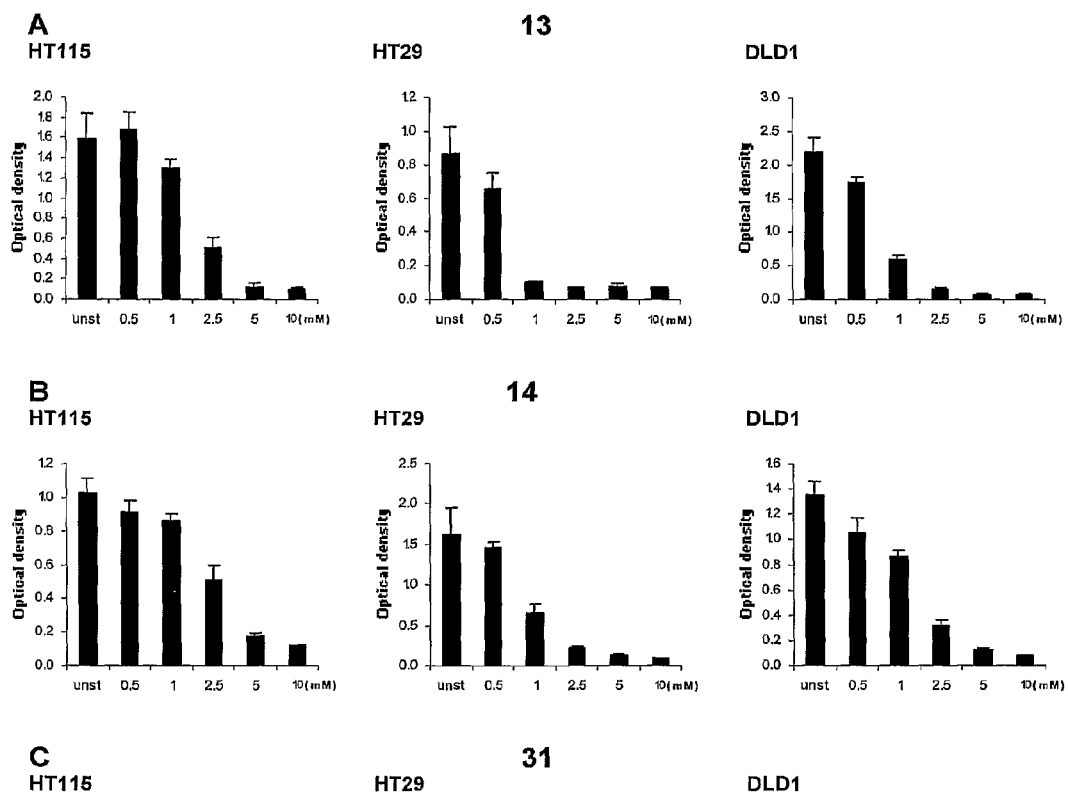

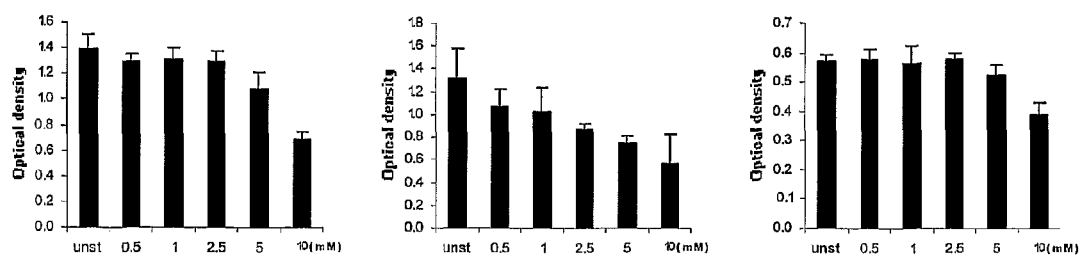
Fig. 7 (cont..)
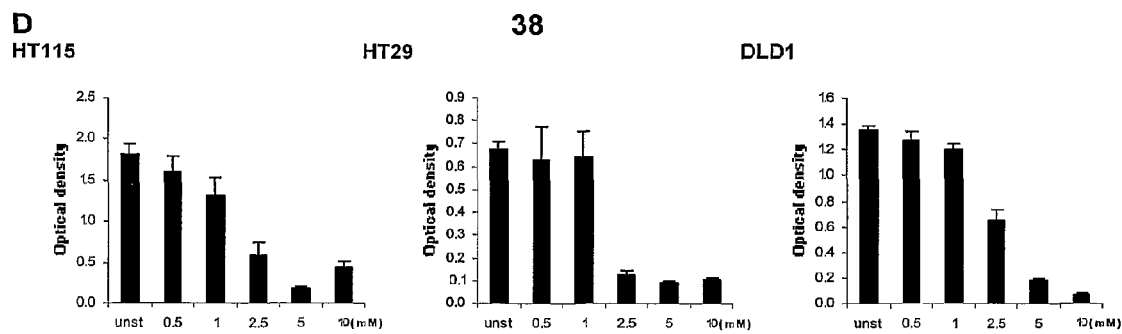

Fig. 8: Proliferation of HT29, HT115 and DLD1 human colon carcinoma cell lines on treatment with 0.5-10 mM novel compound 17, 28 for 48 hours
A
17
HT115
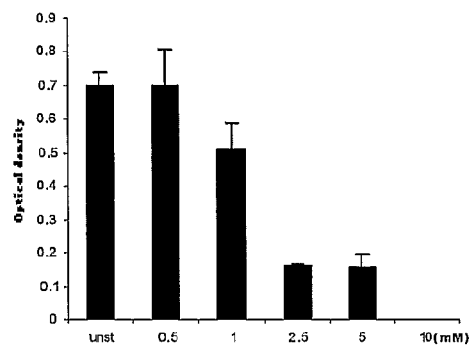
DLD1
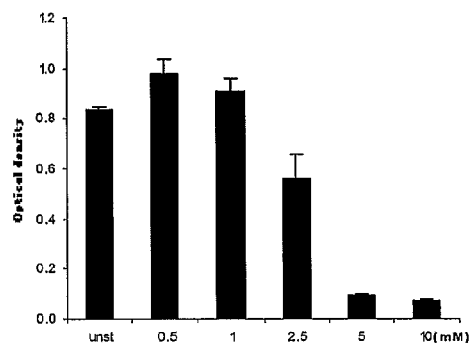
B
26
HT115
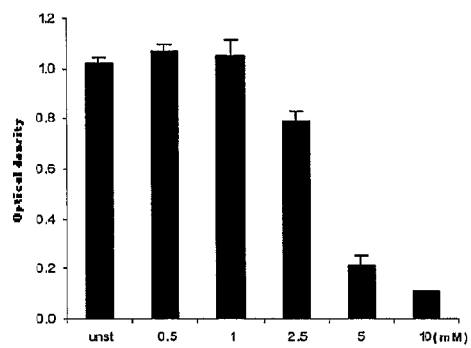
DLD1
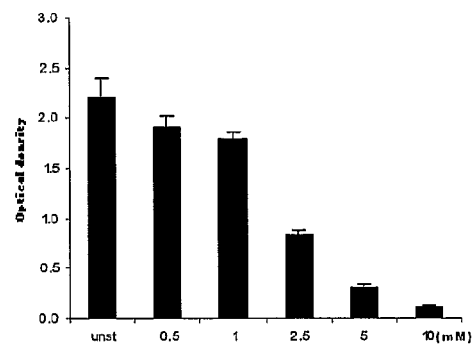

Fig. 9: Cytometric analysis of compound 14's inhibitory effect on the proliferation on DLD-1 cells
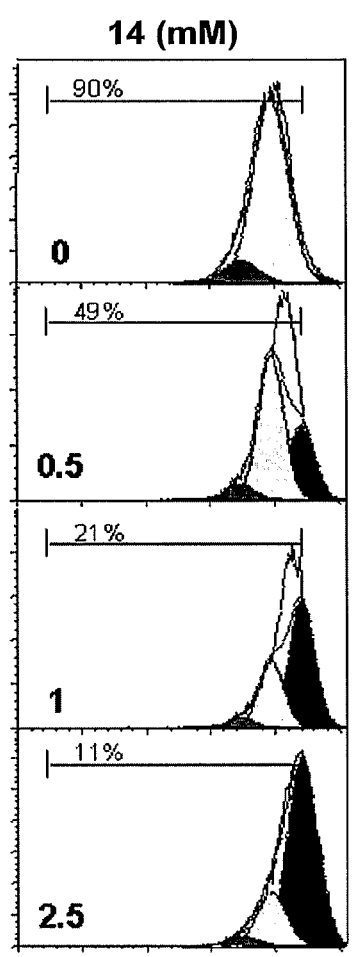

Fig. 10A: Enhancement of DLD1 cell death by compound 14 at 0.75, 1.5 and 3 mM concentrations
Fig. 10B: Reversal of compound 14 effect on DLD-1 cell death
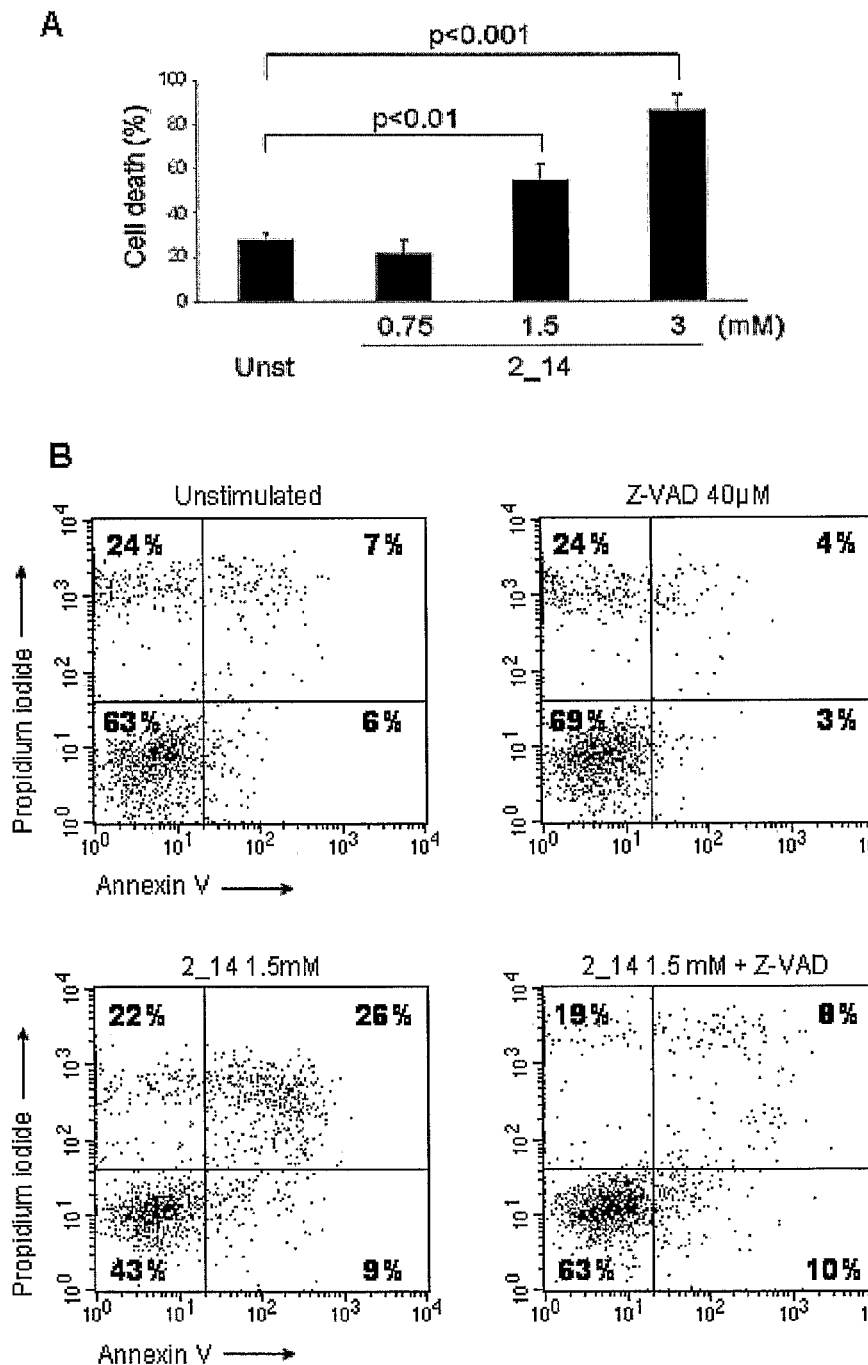

COMPOUNDS AND THEIR SALTS SPECIFIC TO THE PPAR RECEPTORS AND THE EGF RECEPTORS AND THEIR USE IN THE MEDICAL FIELD

RELATED APPLICATIONS

This application is the U.S. National Stage of International Application No. PCT/IE2006/000076, filed 24 Jul. 2006, published in English, and claims priority under 35 U.S.C. §119 or 365 to Italian Application No. RM2005A000390, filed 22 Jul. 2005.

FIELD OF THE INVENTION

The present invention relates to compounds and their salts specific to the PPAR receptors and the EGF receptors and their use in the medical field.

OBJECT OF THE INVENTION

The compounds and their salts according to the present invention can be used advantageously for the prevention and treatment of tumours expressing the PPARγ receptors (Peroxisome Proliferator-Activated Receptors) and the EGF receptors (Epidermal Growth Factor receptors) such as tumours of the: oesophagus, stomach, pancreas, colon, prostate, breast, uterus and appendages, kidneys and lungs. Moreover, the compounds and their salts according to the invention can be used for the treatment of chronic inflammatory diseases, in particular chronic intestinal diseases, such as Crohn's disease and ulcerative rectocolitis.

BACKGROUND TO THE INVENTION

The PPARγ receptors are nuclear receptors (group of approx. 50 transcription factors) which control the expression of many genes that are important for the regulation of lipid metabolism, the synthesis of insulin and the processes of carcinogenesis and inflammation (Bull A W, Arch Pathol Lab Med 2003; 127: 1121-1123) (Koeffler H P, Clin Cancer Res 2003; 9: 1-9) (Youssef J et al., J Biomed Biotec 2004; 3: 156-166).

There are various natural and synthetic agonists which bind to the PPARγ receptors and alter their conformation, giving rise to activation. Natural and synthetic ligands are described in The Lancet 2002; 360:1410-1418.

Recent studies have shown that treatment of tumour cells with ligands of the PPARγ receptors induces a decrease in cellular proliferation, cell differentiation and apoptosis, suggesting potential application of such compounds as agents for preventing carcinogenesis (Osawa E et al., Gastroenterology 2003; 124:361-367).

Other studies have shown that ligands of the PPARγ receptors (e.g. troglitazone) have anti-inflammatory effects and inhibit the mucosal inflammatory response in animal models of IBD (Tanaka T et al., Cancer Res 2001; 61: 2424-2428).

Moreover, evidence has been published very recently that the intestinal anti-inflammatory activity of 5-ASA (5-aminosalicylic acid, mesalazine), the gold standard in the treatment of IBD, is dependent on binding, and consequent activation, of the PPARγ receptors (Rousseaux C et al., J Exp Med 2005; 201: 1205-1215).

The transmembrane receptor with tyrosine-kinase EGF activity is expressed to a very high degree in activated form in various types of neoplasms (Mendelsohn J, Endocr Relat Cancer 2001; 8: 3-9) (Harari P M, Endocr Relat Cancer 2004; 11: 689-708).

Overexpression of the receptor is also related to potential ability of carcinomatous cells to metastasize. In connection to this, it has been demonstrated that EGF promotes the migration and invasiveness of various cell types connected with lesions at the level of interactions with the extracellular matrix (Brunton et al., Oncogene 1997; 14: 283-293).

Numerous studies performed both on experimental animals and in man have established the efficacy of inhibitors of the EGF receptor in controlling proliferation and the spread of tumours (Mendelsohn J, Endocr Relat Cancer 2001; 8: 3-9) (Harari P M, Endocr Relat Cancer 2004; 11: 689-708).

There is no doubt that the intracellular signals triggered by activation of the EGF receptor facilitate the growth and survival of neoplastic cells, contributing to the development of the pathology, and that such signals are essential in determining the ability of tumour cells to spread and colonize remote organs (Mendelsohn J, Endocr Relat Cancer 2001; 8: 3-9) (Kari C et al., Cancer Res 2003; 63: 1-5).

From the foregoing and bearing in mind, moreover, that from the biological standpoint, chronic inflammatory processes play a part in carcinogenesis, it becomes clear that there is a real need for innovative research into new chemical entities which, by their complementary action both on the PPARγ receptors and on the EGF receptors, are able to exert anti-inflammatory and anti-tumour action, of the chemo-preventive, anti-proliferative and anti-metastatic type.

SUMMARY OF THE INVENTION

The present invention relates to novel and inventive medical and therapeutic uses of a series of compounds In so far as any of these compounds are not known, the invention also relates to these compounds.

The present invention provides a novel class of compounds that are suitable for the prevention and treatment of cancer and of chronic inflammation by the modulation of specific receptors such as the PPARγ receptors and the EGF receptors.

Therefore the present invention relates specifically to the compounds of general formula (I)

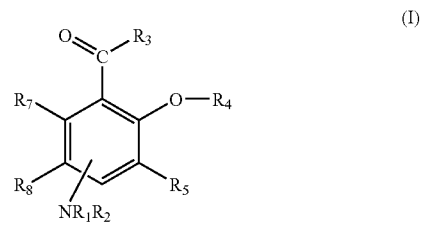

in which $R_1$ and $R_2$, which may be identical or different, are selected from the group comprising H, $-C_nH_{2n-1}$, a linear or branched alkyl group having from 1 to 6 carbon atoms, or together form an aromatic or aliphatic ring with 5 or 6 atoms;

$R_3$ is selected from $-CO-CH$, $-NHOH$, $-OH$, $-OR_6$ in which $R_6$ is a linear or branched alkyl group having from 1 to 6 carbon atoms;

$R_4$ is selected from H, a linear or branched alkyl group having from 1 to 6 carbon atoms, phenyl, benzyl, —$CF_3$ or —$CF_2CF_3$, vinyl or allyl; $R_5$, $R_7$, $R_8$ are hydrogen atoms;

or $R_3$ and $R_4$, $R_4$ and $R_5$, or $R_7$ and $R_8$ together form a ring, fused to the benzene, aromatic or aliphatic ring with 5 or 6 atoms comprising from 1 to 2 heteroatoms selected independently from the group comprising N, O.

The invention also relates to the specific subgroup of compounds of general formula (Ia)

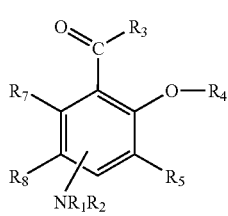

in which $R_1$ and $R_2$, which may be identical or different, are selected from the group comprising H, —CO—$CH_3$, —$C_nH_{2n-1}$, a linear or branched alkyl group having from 1 to 6 carbon atoms, or together form an aromatic or aliphatic ring with 5 or 6 atoms;

$R_3$ is selected from —NHOH, —OH, —$OR_6$ in which $R_6$ is a linear or branched alkyl group having from 1 to 6 carbon atoms;

$R_4$ is selected from —H, a linear or branched alkyl group having from 1 to 6 carbon atoms;

$R_5$, $R_7$, $R_8$ are hydrogen atoms;

or $R_3$ and $R_4$, $R_4$ and $R_5$, or $R_7$ and $R_8$ together form a ring, fused to the benzene, aromatic or aliphatic ring with 5 or 6 atoms comprising from 1 to 2 heteroatoms selected independently from the group comprising N, O.

The aforementioned linear or branched alkyl group of formula (I) or (IIa) having from 1 to 6 carbon atoms can be selected from —$CH_3$, —$C_2H_5$, isopropyl, propyl, $C_nH_{2n-1}$.

The present invention also relates to compounds as recited in formulae (I) and (Ia) except without allowing for where $R_3$=—$COCH_3$. There is a theoretical possibility that some acetyl derivatives such as at least some of those when $R_3$=—$COCH_3$ may be inactive, since N-acetylation is the metabolic detoxification system for aromatic amines. The theoretical possibility arises from the observation that the inactive metabolite of 5-ASA is N-acetyl 5-ASA.

In some embodiments of both formula (I) and (Ia) the invention, $R_7$ and $R_8$ may not form a ring. Thus $R_3$ and $R_4$ or $R_4$ and $R_5$ may together form a ring, fused to the benzene, aromatic or aliphatic ring with 5 or 6 atoms comprising from 1 to 2 heteroatoms selected independently from the group comprising N, O. In some embodiments compounds 29, 36 and 37 are excluded. In some embodiments of both formula (I) and (Ia) the invention, $R_7$ and $R_8$ may not form a ring except when $R_4$ is $CH_3$. In some embodiments of both formula (I) and (Ia) the invention, $R_7$ and $R_8$ may not form a ring when $R_4$ is selected from H. In some embodiments, the invention relates to the ketolenes provided by the invention. In some embodiments, compound 29 is excluded.

In some embodiments, one or more compounds selected from the group consisting of compounds 5, 6, 7, 8, 9, 12, 16, 18, 19, 24, 25, 27, 30, and 41 are excluded.

In some embodiments of both formula (I) and (Ia) the invention, $R_1$ and $R_2$ may not form a ring. Thus $R_1$ and $R_2$, which may be identical or different, may be selected from the group comprising —H, —$C_nH_{2n-1}$, a linear or branched alkyl group having from 1 to 6 carbon atoms. In some embodiments compound 41 is excluded.

In some embodiments of both formula (I) and (Ia) of the invention, $R_4$ may not be branched. Thus $R_4$ may be selected from H, a linear alkyl group having from 1 to 6 carbon atoms; $R_5$, $R_7$, $R_8$ are hydrogen atoms. In such embodiments, compound 30 and 31 are excluded. In some embodiments, $R_4$ may not be branched when the amino group is at position 4' on the phenyl ring. In such embodiments, compound 30 is excluded. In some embodiments, the linear alkyl group may have only 1 carbon atom (i.e., $CH_3$).

In some embodiments of both formula (I) and (Ia) the invention, $R_1$ and $R_2$ are —H. In some embodiments compounds 6, 9, 24, 27, 38 and 41 are excluded.

In some embodiments of both formula (I) and (Ia) of the invention, $R_2$ may not be different to $R_1$.

In some embodiments of both formula (I) and (Ia) of the invention, when $R_3$ is —OH, $R_4$ is selected from the group consisting —H, a branched alkyl group having from 1 to 6 carbon atoms, or $R_3$ and $R_4$, together form a ring, fused to the benzene, aromatic or ring with 5 or 6 atoms comprising from 1 to 2 heteroatoms selected independently from the group comprising N, O. In some embodiments, the branched alkyl group may be —$CH(CH_3)_2$. In some embodiments, the branched alkyl group may be —$CH(CH_3)_2$ at the $R_8$ position. In some embodiments, $R_3$ and $R_4$ form a 5-membered aliphatic ring with a single O atom. In some embodiments (such as the ones described in this paragraph), compounds 7, 8, 18, 19, 42 are excluded.

In some embodiments of both formula (I) and (Ia) of the invention, when $R_3$ is —OH and $R_4$ is —H, the group $NR_1R_2$ cannot be at the 4' position (and should be at $R_5$ or $R_8$). In some embodiments, this may be particularly the case where $R_1$ and $R_2$ are —$CH_3$. In some embodiments compound 24 is excluded.

In some embodiments of both formula (I) and (Ia) of the invention, $R_1$ and $R_2$ are the same. In some embodiments compounds 9 and 12 are excluded.

In some embodiments of both formula (I) and (Ia) of the invention, when $R_3$ is —OH and $R_4$ is —H, the group —$NR_1R_2$ cannot be at the $R_5$ (and should be at the $R_8$ position). In some embodiments, this may be where $R_1$ and $R_2$ are —H. In some embodiments compound 6 is excluded.

In some embodiments of both formula (I) and (Ia) of the invention, when $R_3$ is —NHOH, $R_4$ is a linear or branched alkyl group having from 1 to 6 carbon atoms, (or, if formula (I) phenyl, benzyl, —$CF_3$ or —$CF_2CF_3$, vinyl or allyl), $R_3$ and $R_4$, together form a ring, fused to the benzene, aromatic or aliphatic ring with 5 or 6 atoms comprising from 1 to 2 heteroatoms selected independently from the group comprising N, O. In some embodiments compound 7 is excluded.

In some embodiments of both formula (I) and (Ia) of the invention, when $R_3$ is —NHOH, and $R_4$ is a linear or branched alkyl group having from 2 carbon atoms, the group —$NR_1R_2$ may not be at the 4' position and can be at the $R_8$ position. In some embodiments compound 25 is excluded.

In some embodiments of both formula (I) and (Ia) of the invention, when $R_3$ is —NHOH, and $R_4$ is —H, the group —$NR_1R_2$ may not be at $R_8$ and must be at the 4' position. In some embodiments compound 5 is excluded.

According to one embodiment, $R_3$ and $R_4$ of the compounds of formula (I) and (Ia) can form a ring according to the following formula (II)

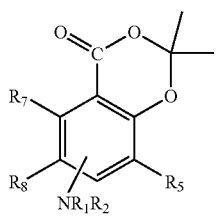

(II)

while $R_1$, $R_2$, $R_5$, $R_7$ and $R_8$ are defined above.

According to another embodiment $R_4$ and $R_5$ of the compounds of formula (I) and (Ia) can form a ring according to the following formula (III)

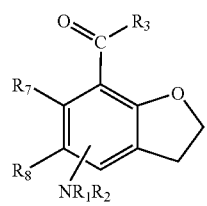

(III)

while $R_1$, $R_2$, $R_3$, $R_7$ and $R_8$ are defined above.

According to a further embodiment $R_7$ and $R_8$ of the compounds of formula (I) and (Ia) can form a ring according to the following formula (IV) or (V)

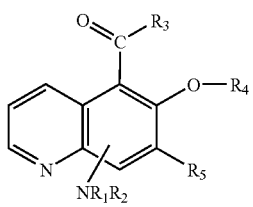

(IV)

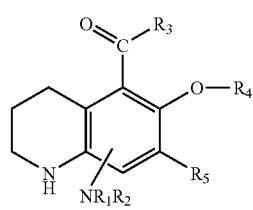

(V)

while $R_1$, $R_2$, $R_3$, $R_4$ and $R_5$ are defined above.

In particular, the compounds of formula (I) and (Ia) according to the present invention can be selected from the group comprising 4-amino-N-hydroxy-2-methoxybenzamide (compound 13)
5-amino-N-hydroxy-2-methoxybenzamide (compound 14)
5-amino-2,3-dihydrobenzofuran-7-carboxylic acid (compound 17)
5-amino-2-ethoxy-N-hydroxybenzamide (compound 26)
6-amino-2,2-dimethyl-4H-benzo[1,3]dioxin-4-one (compound 28)
1,2,3,4-tetrahydro-6-hydroxyquinoline-5-carboxylic acid (compound 29)
5-amino-2-isopropoxybenzoic acid (compound 31)
6-methoxy quinoline-5-carboxylic acid (compound 36)
6-methoxy-1,2,3,4-tetrahydroquinoline-5-carboxylic acid (compound 37)
5-diisopropylaminosalicylic acid (compound 38)
4-diisopropylaminosalicylic acid (compound 42).

The present invention also provides for compounds wherein $R_1$ and $R_2$, are selected from the group consisting of —H and —CH(CH$_3$)$_2$. $R_1$ and $R_2$ may both be identical. In some embodiments, $R_1$ and $R_2$ may be —CH(CH$_3$)$_2$.

One example comprises the following structure (compound 38):

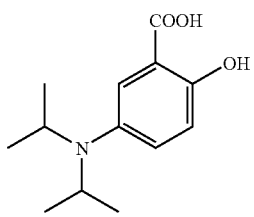

In other embodiments of the invention, $R_1$ and $R_2$, are both —H.

The present invention also provides for compounds wherein $R_3$ is selected from the group consisting of —NHOH and —OH. In some embodiments $R_3$ may be —NHOH. One example comprises the following structure (compound 13):

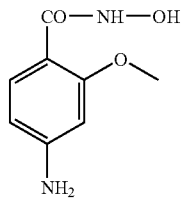

A further example comprises the following structure (compound 14):

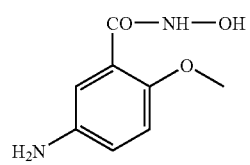

A further example comprises the following structure (compound 26):

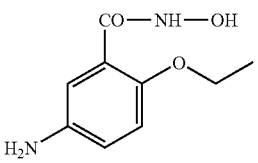

In some embodiments of the invention, $R_3$ may be —OH.

A suitable example comprises the following structure (compound 17):

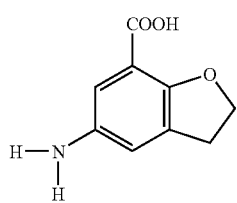

A further example comprises the following structure (compound 31):

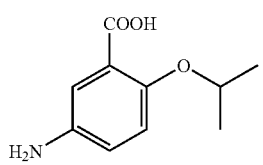

In some embodiments of the invention, $R_4$ may be —H. In some embodiments of the invention, $R_4$ may be $CH_3$. In some embodiments of the invention, $R_4$ may be, —$CH_2CH_3$. In some embodiments of the invention, $R_4$ may be —$CH(CH_3)_2$.

A further example comprises the following structure (compound 28):

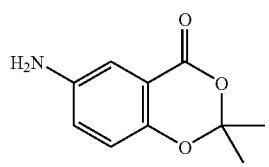

In some embodiments of the invention, $R_3$ and $R_4$ may together form an aliphatic ring, fused to the benzene, of 5 or 6 atoms comprising one hetero atom O (oxygen).

The compounds according to the invention can be used advantageously in the medical field.

Therefore the present invention further relates to a pharmaceutical composition comprising one or more compounds according to the invention as active principles in combination with one or more pharmaceutically acceptable excipients or adjuvants.

Furthermore, the present invention relates to the use of the compounds according to the invention for the preparation of a medicinal product for the prevention and treatment of tumours expressing PPARγ receptors and EGF receptors such as tumour of the oesophagus, stomach, pancreas, colon, prostate, breast, of the uterus and appendages, of the kidneys and of the lungs.

Moreover, the invention relates to the use of the compounds according to the present invention for the preparation of a medicinal product for the treatment of chronic inflammatory diseases such as Crohn's disease and ulcerative rectocolitis. The present invention also relates to methods of treatment of humans and/or mammals (including rodents, farm animals, domestic pets, mice, rats, hamsters, rabbits, dogs, cats, pigs, sheep, cows, horses).

In particular, apart from the specific compounds mentioned above, the following compounds can be used for the applications described above:

5-aminosalicylo-hydroxamic acid (compound 5)
3-dimethylaminosalicylic acid (compound 6)
2-methoxy-4-aminobenzoic acid (compound 7)
2-methoxy-5-aminobenzoic acid (compound 8)
5-methylaminosalicylic acid (compound 9)
4-methylaminosalicylic acid (compound 12)
4-acetylaminosalicylic acid (compound 16)
2-ethoxy-4-aminobenzoic acid (compound 18)
2-ethoxy-5-aminobenzoic acid (compound 19)
4-dimethylaminosalicylic acid (compound 24)
2-ethoxy-4-aminobenzoylhydroxamic acid (compound 25)
6-hydroxyquinoline-5-carboxylic acid (compound 27)
2-(2-propyl)oxy-4-aminobenzoic acid (compound 30)
4-(1-piperazinyl)salicylic acid (compound 41).

The molecules of the present invention were derived from molecular modeling work using mesalazine as a basis and all chemically feasible variations were evaluated in order to achieve the best score (affinity and activation of the receptor) in computer docking experiments. Consequently, it is believed that the compounds of the present invention that show comparable function and/or activity to mesalazine do so through similar biological pathways. It is believed that similar characteristics to mesalazine inherent in the molecules of the invention confer upon the molecules a similar activity in relation to the EGF pathway.

The experiments given herein make good models for use in the prediction of the use of the compounds in the various medical fields already discussed. The models used give meaningful results regardless of the mechanism of action.

In addition to the above mentioned compounds, the present invention provides for the use of the following compounds (compound number follows prefix "2_"):

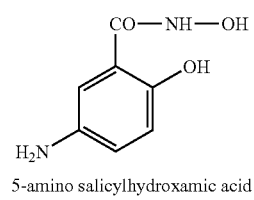

5-amino salicylhydroxamic acid

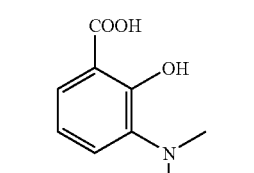

3-dimethylamino salicylic acid

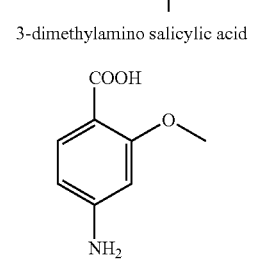

2-methoxy-4-amino benzoic acid

-continued

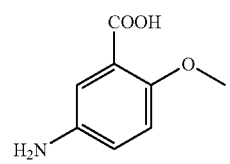
2-methoxy-5-amino benzoic acid
2_08

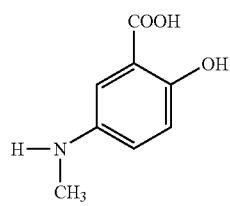
5-methylamino salicylic acid
2_09

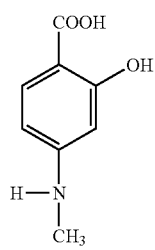
4-methylamino salicylic acid
2_12

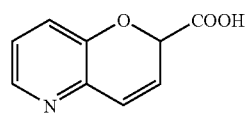
(R,S) 5-oxa-quinoline-6-carboxylic acid
2_15

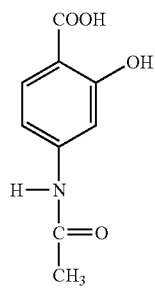
4-acetylamino salicylic acid
2_16

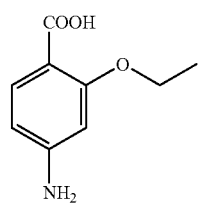
2-ethoxy-4-aminobenzonic acid
2_18

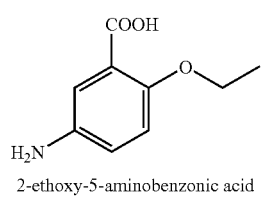
2-ethoxy-5-aminobenzonic acid
2_19

-continued

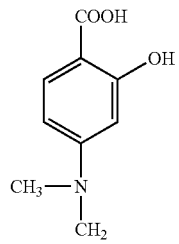
4-dimethylamino salicylic acid
2_24

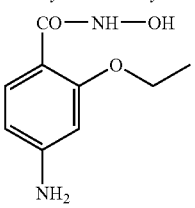
2-ethoxy-4-amino benzoylhydroxamic acid
2_25

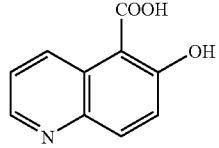
6-hydroxy-quinoline-5-carboxylic acid
2_27

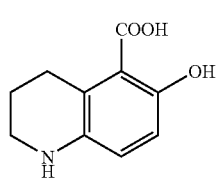
1,2,3,4-tetrahydro-6-hydroxy quinoline-5-carboxylic acid
2_29

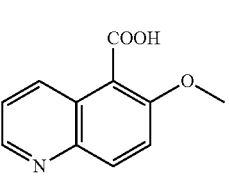
6-methoxy quinoline-5-carboxylic acid
2_36

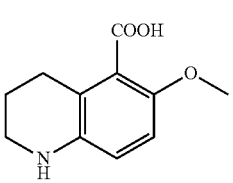
6-methoxy-1,2,3,4,-tetrahydro quinoline-5-carboxylic acid
2_37

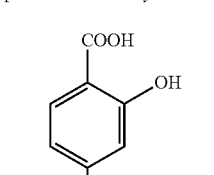
mw  221.25604
4-(1-piperazinyl) salicylic acid
2_41

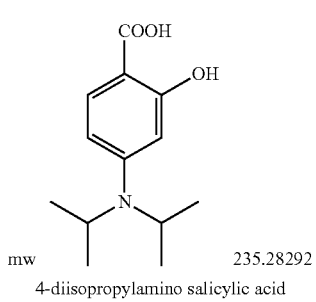

mw 235.28292
4-diisopropylamino salicylic acid

The present invention will now be described for purposes of illustration, but without limiting it, according to its preferred embodiments, with particular reference to the diagrams in the appended drawings.

BRIEF DESCRIPTION OF THE DRAWINGS AND TABLE

FIG. 1A shows the structures of compounds 13, 14, 17, 26, 31 and 38.

FIG. 1B shows the activation of the PPARγ receptors by molecules 17 and 31 relative to cells treated with 5-ASA and rosiglitazone. The HT-29 STD cells transfected with the response element for PPARγ (2XCYP) and treated with molecules 17 and 31 (30 mM) show induction of about twice the activity of the reporter gene indicating the capacity of 5-ASA and novel compounds 17 and 31 to induce activation of the PPARγ; the results are expressed as factor of increase in activation (mean±SEM) relative to the untreated cells. The activations for compounds 13, 14, 26 and 38 are also shown.

FIG. 2 shows the increase in expression of the PPARγ protein by the epithelial cells induced by compounds 17, 26 and 31; the level of expression of the PPARγ protein was evaluated by western blot in untreated HT-29 cells (control) and after 24 hours of treatment with the novel compounds or 5-ASA (30 mM) or rosiglitazone ($10^{-5}$M) used as positive controls. The values of optical density of the PPARγ were calculated for each condition in proportion to the quantity of the β-actin internal control in the same sample.

FIG. 3 shows the inhibition of proliferation of epithelial cells by compounds 17 and 31; similarly to 5-ASA (30 mM) and to rosiglitazone ($10^{-5}$M), compounds 17 and 31 inhibit proliferation of the HT-29 STD cells, tested by staining with nuclear Ki-67 (light grey) relative to the cells incubated with the culture medium only (control); the nuclei were stained blue (dark grey in figure) with Hoechst 33342 solution; the results are expressed as average number of cells counted in one experiment.

FIG. 4 shows the induction of apoptosis of epithelial cells by compound 31; similarly to 5-ASA (30 mM) and rosiglitazone ($10^{-5}$M), molecule 31 induced apoptosis identified in the TUNEL assay in HT-29 STD cells. Spontaneous apoptosis of 3% was observed in the untreated HT-29 cells; the results are expressed as average number of cells counted in one experiment.

FIG. 5A shows docking simulation of the manner of binding of various compounds to the PPARγ; compared with the interaction of the novel compounds (from 13 to 38) stained according to the type of atom in the ligand binding domain (LBD) represented by a white surface in the X-ray crystal structure of the PPARγ; description of the key hydrogen binding interactions between the novel molecules and the PPARγ.

FIG. 5B shows a detailed docking simulation of the manner of binding of mesalazine to the PPARγ receptor.

FIG. 5C shows a more detailed docking simulation of the manner of binding of compound 17 to the PPARγ receptor.

FIG. 5D shows a more detailed docking simulation of the manner of binding of compound 31 to the PPARγ receptor.

FIG. 6 shows the analysis of PPARγ activity of compounds 13, 14, 17, 26, 28, 31 and 38, in transfected HT-29 cells. This shows that the new molecules increase the reporter gene activity, thereby displaying an activity similar or superior to 5-ASA.

Figure 2:
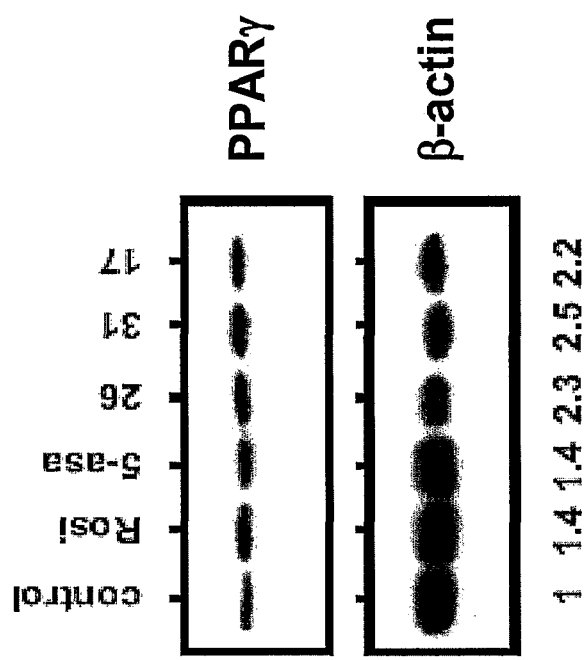

FIGS. 7-8 show the effect of the specified substances on the proliferation of three different human colon carcinoma cell lines (i.e. HT29, HT115 and DLD1). The cells were treated with increasing concentrations of substances (0.5-10 mM)) for 48 hours and the proliferation was determined by using a colorimetric assay for the measurement of BrdU incorporation. The optical density (OD) was determined at 450 nm using an ELISA reader. Data indicate the mean±SD of 3 separate experiments.

FIG. 9 shows the flow cytometric analysis of compound 14's inhibitory effect on the proliferation on DLD-1 cells. One of three representative experiments in which similar results were obtained is shown. Cells were labeled with CFSE and their proliferative fraction was calculated after 48 hours culture by flow cytometry.

FIG. 10A shows that compound 14 significantly enhances DLD1 cell death at concentrations of 1.5 (p<0.01) and 3 mM (p<0.001). DLD1 were either left unstimulated (Unst) or treated with compound 14 for 48 hours. Data express mean±SD of 3 separate experiments and indicate the percentage of cell death as assessed by FACS analysis of AV and/or PI-positive cells.

FIG. 10B shows Z-VAD, a pan-caspase inhibitor, reverses the effect of compound 14 on DLD-1 cell death. The results are displayed as biparametric histograms of Annexin-V-FITC and PI fluorescences allowing discrimination between viable cells, apoptotic cells with an intact membrane and cells undergoing secondary necrosis. One of three representative experiments in which similar results were obtained is shown.

Table 1. Percentages of DLD-1 cell inhibition by graded doses (0.5-10 mM) of the specified compounds. Cells were cultured in the presence or absence of the compounds, and cell growth was then assessed by the calorimetric (BrdU) assay after 48 hours culture.

EXAMPLE 1

Method of Preparing
4-Amino-N-hydroxy-2-methoxybenzamide
(Compound 13)

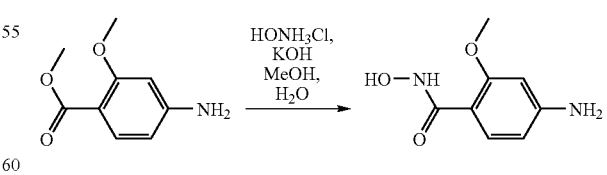

Methyl 2-methoxy-4-aminobenzoate (10 g, 55.25 mmol) and hydroxylamine hydrochloride (15.36 g, 221 mmol) were taken up in MeOH (80 ml) and a solution of KOH (15.4 g, 275 mmol) in MeOH (55 ml) was added carefully. The resultant mixture was stirred at reflux for 36 hrs. The volatiles were removed in vacuo. The residue was taken up in 1M NaOH (50 ml) and washed with ethyl acetate (EtOAc, 50 ml). Concentrated HCl was added slowly until precipitation of a solid (pH was 10). The solid was filtered off, washed with H$_2$O, then methyl-tert-butyl ether (MTBE) and dried under vacuum. $^1$H NMR showed the solid contained approx. 1/3 molar equivalent of ethyl acetate. The solid was taken up in 1M NaOH (100 ml) and the EtOAc was removed in vacuo. Concentrated HCl was added carefully until precipitation of a solid (pH was 8). The solid was collected by filtration, washed with H$_2$O, then MTBE and dried under vacuum to give 4.67 g (47%) of the title compound as a dark red solid.

$^1$H NMR (δ, 250 MHz, d$_6$-DMSO): 3.75 (s, 3-H, OMe), 5.64 (s, 2-H, NH$_2$), 6.14 (dd, 1-H, aromatic), 6.18 (brs, 1-H, aromatic), 7.48 (d, 1-H, aromatic), 8.73 (s, 1-H, NH), 10.06 (s, 1-H, OH).

EXAMPLE 2

Method of Preparing
5-Amino-N-hydroxy-2-methoxybenzamide
(Compound 14)

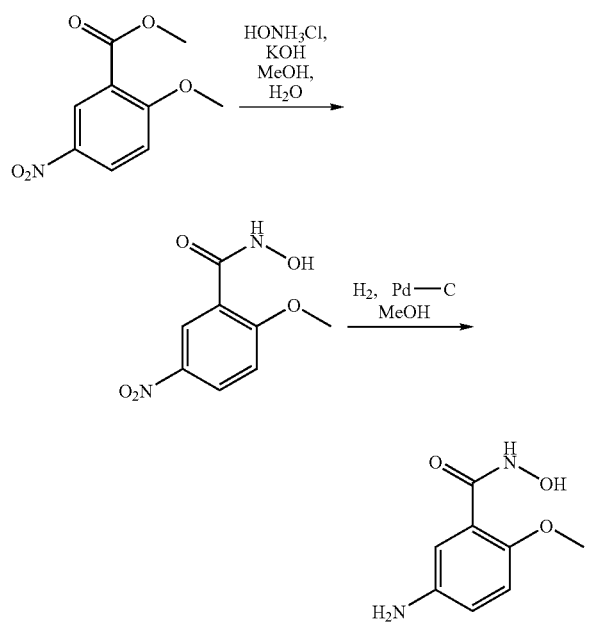

Methyl 2-methoxy-5-nitrobenzoate (10 g, 47.39 mmol) and hydroxylamine hydrochloride (13.17 g, 189.56 mmol) were taken up in MeOH (100 ml) and a solution of KOH (13.27 g, 236.95 mmol) in MeOH (55 ml) was added carefully. Note—an exothermic reaction was observed; solids initially dissolved, then a solid precipitated out of solution. TLC (run in EtOAc) of an acid washed aliquot showed a trace of the starting benzoate and a new product. H$_2$O (100 ml) was added and any undissolved solid collected by filtration off, washed with isopropyl alcohol (IPA) and dried in vacuo to give 10.23 g (>100%) of N-hydroxy-2-methoxy-5-nitrobenzamide as a white solid.

$^1$H NMR (δ, 250 MHz, MeOD): 4.18 (3-H, OMe), 7.43 (d, 1-H, aromatic), 8.39 (dd, 1-H, aromatic), 8.83 (d, 1-H, aromatic)

N-Hydroxy-2-methoxy-5-nitrobenzamide (approx. 47.39 mmol) was taken up in IMS (500 ml) and 10% Pd on C (50% wet) (1 g) was added. The mixture was hydrogenated at 50 psi for 1.5 hr, then filtered through celite, and the celite washed with 2M NaOH (200 ml). The MeOH was removed in vacuo and the resulting aqueous residue washed with MTBE (100 ml). The pH of the aqueous was lowered to 7 by the careful addition of concentrated HCl, and the resulting precipitated solid collected by filtration, washed with H$_2$O, then MTBE and dried under high vacuum overnight to give 5.33 g of the title compound (62%) as a light brown solid.

$^1$H NMR (δ, 250 MHz, d$_6$-DMSO): 4.09 (3-H, OMe), 7.02 (1-H, aromatic), 7.18 (1-H, aromatic), 7.28 (1-H, aromatic), 9.36 (1-H, NH), 10.83 (1-H, OH).

EXAMPLE 3

Method of Preparing
5-Amino-2,3-dihydrobenzo[b]furan-7-carboxylic
Acid (Compound 17)

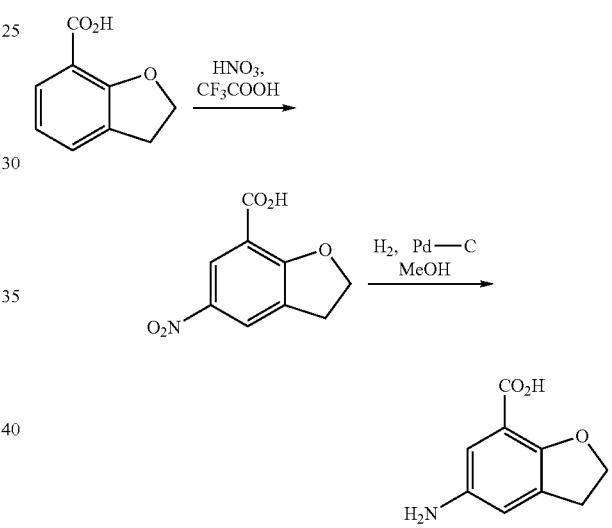

Nitric acid (9 ml) was added to a cooled (ice bath) solution of 2,3-dihydrobenzo[b]furan-7-carboxylic acid (5.1 g, 31 mmol) in trifluoroacetic acid (45 ml). After 4 hours the mixture was quenched into ice-water (150 ml) and the mixture filtered to give 5-nitro-2,3-dihydrobenzo[b]furan-7-carboxylic acid, which was washed with water and used crude (wet) in the next stage.

$^1$H NMR (δ, 250 MHz, CD$_3$OD): 3.70 (2H, t, 8.7 Hz), 5.21 (2H, t, 8.9 Hz), 8.67 (1H, d, 2.7 Hz), 8.83 (1H, d, 2.4 Hz)

The crude 5-nitro-2,3-dihydrobenzo[b]furan-7-carboxylic acid was dissolved in the minimum amount of methanol (1.3 L) and nitrogen was bubbled through the solution for 20 minutes. A mixture of 5% palladium on charcoal (1.0 g) in water (20 ml) was added and the mixture loaded into a 2 L autoclave. After 2 sequential evacuation-N$_2$ purges the vessel was charged to 5 bar H$_2$ and stirred for 4 days. The mixture was flushed with nitrogen, filtered through celite and concentrated to give 5-amino-2,3-dihydrobenzo[b]furan-7-carboxylic acid (3.5 g, 19.5 mmol, 63% over 2 steps)

$^1$H NMR (δ, 250 MHz, CD$_3$OD): 3.46 (2H, t, 8.5 Hz), 4.85 (2H, t, 8.7 Hz), 7.19 (1H, br s), 7.27 (1H, br s)

EXAMPLE 4

Method of Preparing
5-Amino-2-ethoxy-N-hydroxybenzamide
(Compound 26)

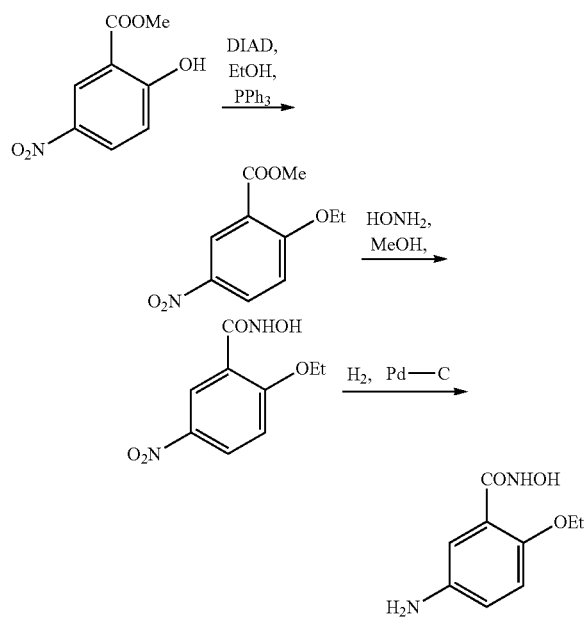

Step 1

Methyl 2-hydroxy-5-nitrobenzoate (11.82 g, 60 mmol), triphenylphosphine (17.29 g, 66 mmol) and EtOH (3.03 g, 3.85 ml, 66 mmol) were taken up in THF (150 ml) and cooled in ice. Di-isopropyl-azodicarboxylate (8.31 g, 10 ml, 66 mmol) was added carefully, and the reaction was stirred at RT for 1 hr. The reaction was concentrated in vacuo, and the residue was triturated with EtOAc (50 ml). The solid thus formed was collected by filtration, washed with MTBE and dried in vacuo to give 12.2 g of crude methyl 2-ethoxy-5-nitrobenzoate. The filtrate was evaporated in vacuo, and the resulting residue was triturated with EtOAc (25 ml). The resulting solid was collected by filtration, washed with MTBE and dried in vacuo to give 6.31 g of a second crop of crude methyl 2-ethoxy-5-nitrobenzoate. The combined portions of methyl 2-ethoxy-5-nitrobenzoate were taken up in hot IPA (50 ml) and cooled to RT. The resulting solid was collected by filtration, washed with MTBE and dried in vacuo to give pure methyl 2-ethoxy-5-nitrobenzoate (5.49 g, 40.5%) as a yellow solid.

$^1$H NMR ($\delta$, 250 MHz, DMSO-$d_6$): 1.38 (3H, t, $CH_3CH_2O$), 3.85 (3H, s, OMe), 4.28 (2H, q, $CH_3CH_2O$), 7.38 (1H, d, aromatic), 8.40 (1H, dd, aromatic), 8.48 (1H, d, aromatic).

Step 2

Methyl 2-ethoxy-5-nitrobenzoate (6.099 g, 26.99 mmol) and 50% wt/v aqueous hydroxylamine (40 ml) were taken up in MeOH (100 ml) and stirred at RT overnight. The resulting precipitated yellow solid was collected by filtration, washed with IPA and dried in vacuo. The filtrate was evaporated in vacuo and the residue was triturated with IPA (25 ml). The solid that didn't dissolve was filtered off, washed with a minimum quantity of IPA and dried in vacuo. The two crops of solid were suspended in $H_2O$ (300 ml) and the pH was lowered to 2 by careful addition of concentrated HCl. The solid was filtered off, washed with MTBE and dried in vacuo to give 3.9 g of crude 2-ethoxy-5-nitro-N-hydroxybenzamide. The IPA mother liquors from above were combined with the crude 2-ethoxy-5-nitro-N-hydroxybenzamide and evaporated in vacuo. The residue was triturated with $CH_2Cl_2$ (25 ml) and the solid was filtered off and dried in vacuo to give 2-ethoxy-5-nitro-N-hydroxybenzamide (2.39 g, 39%) as a yellow solid.

$^1$H NMR ($\delta$, 250 MHz, DMSO-$d_6$): 1.39 (t, 3-H, $CH_3CH_2O$), 4.28 (q, 2-H, $CH_3CH_2O$), 7.34 (d, 1-H, aromatic), 8.38 (dd, 1-H, aromatic), 8.48 (d, 1-H, aromatic), 9.32 (s, 1-H, NH), 10.79 (s, 1-H, OH).

Step 3

2-Ethoxy-5-nitro-N-hydroxybenzamide (2.39 g, 1.06 mmol) was suspended in EtOH (50 ml) and 10% Pd on carbon (wet basis) (240 mg) was added. The mixture was hydrogenated at 50 psi for 1.5 hrs. MeOH (50 ml) was added and the mixture was filtered through celite. The volatiles were removed in vacuo and the residue was taken up in IPA (50 ml). The mixture was heated at 60° C. for 0.5 hr then stood at RT overnight. The precipitated solid was collected by filtration, washed with MTBE and dried in vacuo to give 1.51 g of 5-amino-2-ethoxy-N-hydroxybenzamide (73%) as an off-white solid.

$^1$H NMR ($\delta$, 250 MHz, DMSO-$d_6$): 1.28 (t, 3-H, $CH_3CH_2O$), 3.97 (q, 2-H, $CH_3CH_2O$), 4.81 (s, 2-H, $NH_2$), 6.61 (dd, 1-H, aromatic), 6.80 (d, 1-H, aromatic), 6.87 (d, 1-H, aromatic), 9.00 (s, 1-H, NH), 10.35 (s, 1-H, OH).

EXAMPLE 5

Method of Preparing
6-Amino-2,2-dimethyl-4H-benzo[1,3]dioxin-4-one
(Compound 28)

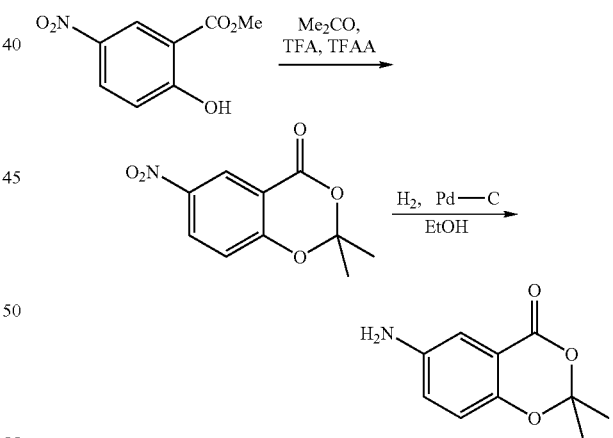

Step 1

5-Nitrosalicylic acid (25 g, 136.6 mmol) was taken up in acetone (20 ml) and trifluoroacetic acid (150 ml) and trifluoroacetic anhydride (50 ml) were added. The mixture was heated at reflux. After 1 hr more acetone (30 ml) was added, and the reaction was heated at reflux for 48 hrs. The reaction was cooled to RT and the volatiles were removed in vacuo. The resulting brown oil was dissolved in $CH_2Cl_2$ (400 ml) and washed with 1:1 $H_2O$/saturated $NaHCO_3$ (400 ml). The aqueous phase was extracted with $CH_2Cl_2$ (2×200 ml), and the combined organic layers were dried ($MgSO_4$) and evaporated in vacuo. The solid residue was triturated with pentane (150 ml), collected by filtration, washed thoroughly with pentane and dried in vacuo to give 6-nitro-2,2-dimethyl-4H-benzo[1,3]dioxin-4-one (27.84 g, 91%) as a dark yellow solid.

$^1$H NMR (δ, 250 MHz, CDCl$_3$): 1.79 (s, 6-H, CH$_3$), 7.13 (d, 1-H, aromatic), 8.43 (dd, 1-H, aromatic), 8.87 (d, 1-H, aromatic).

Step 2

6-Nitro-2,2-dimethyl-4H-benzo[1,3]dioxin-4-one (5 g, 22.42 mmol) was taken up in EtOH (35 ml) and 10% Pd on C (wet basis) (2.37 g) was added. The mixture was hydrogenated at 50 psi for 1 hr. The mixture was filtered through celite and the volatiles were removed in vacuo. IPA (50 ml) was added and the mixture was heated at 60° C. for 5 mins then allowed to cool to RT. The resulting solid was filtered off, washed with MTBE and dried in vacuo to give 2.93 g of 6-amino-2,2-dimethyl-4H-benzo[1,3]dioxin-4-one (68%) as a yellow solid.

$^1$H NMR (δ, 250 MHz, CDCl$_3$): 1.71 (s, 6-H, CH$_3$), 6.80 (d, 1-H, aromatic), 6.93 (dd, 1-H, aromatic), 7.26 (d, 1-H, aromatic)

EXAMPLE 6

Method of Preparing 5-Amino-2-isopropoxybenzoic Acid (Compound 31)

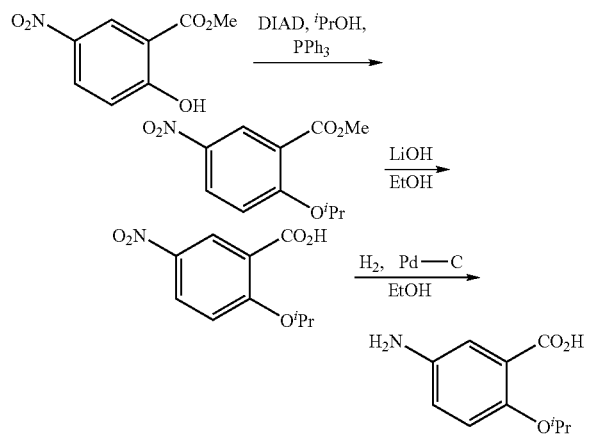

Methyl 2-hydroxy-5-nitrobenzoate (11.82 g, 60 mmol), triphenylphosphine (17.29 g, 66 mmol) and $^i$PrOH (3.96 g, 5 ml, 66 mmol) were taken up in THF (150 ml) and cooled in ice. Di-isopropyl-azodicarboxylate (8.31 g, 10 ml, 66 mmol) was added carefully, and the reaction was stirred at RT overnight. The volatiles were removed in vacuo and the residue treated with EtOAc (50 ml). The solids that didn't dissolve were removed by filtration, and the filtrate evaporated to dryness in vacuo. The residue was purified by column chromatography to give methyl 2-isopropoxy-5-nitrobenzoate (6.92 g, 48.5%) as a yellow oil.

Methyl 2-isopropoxy-5-nitrobenzoate (6.92 g, 28.95 mmol) was taken up in THF/H$_2$O (35 ml of each) and LiOH (1.39 g, 57.9 mmol) was added. The mixture was stirred at RT overnight then the pH was lowered to 1 by the addition of concentrated HCl and the product extracted in ethyl acetate (50 ml). The organic layer was dried (MgSO$_4$) and evaporated to give 2-isopropoxy-5-nitrobenzoic acid (6.02 g, 92.5%) as a yellow solid. $^1$H NMR (δ, 250 MHz, DMSO-d$_6$): 1.32 (d, 6-H, CH$_3$), 4.88 (septet, 1-H, CH), 7.37 (d, 1-H, aromatic), 8.32 (dd, 1-H, aromatic), 8.40 (d, 1-H, aromatic), 13.13 (s, 1-H, CO$_2$H). 2-Isopropoxy-5-nitrobenzoic acid (6.02 g, 26.75 mmol) was suspended in EtOH (100 ml) and 10% Pd on C (wet basis) (600 mg) was added. The mixture was hydrogenated at 50 psi for 2 hrs. The mixture was filtered through celite and the volatiles were removed in vacuo. The residue was triturated with IPA, and the resulting solid filtered off, washed with MTBE and dried in vacuo to give 4.15 g of 5-amino-2-isopropoxybenzoic acid (79.5%) as a pale yellow solid.

$^1$H NMR (δ, 250 MHz, DMSO-d$_6$): 1.21 (d, 6-H, CH$_3$), 4.33 (septet, 1-H, CH), 7.68 (dd, 1-H, aromatic), 6.84 (d, 1-H, aromatic), 6.89 (d, 1H, aromatic)

EXAMPLE 7

Method of Preparing 4-Diisopropylaminosalicylic Acid (Compound 38)

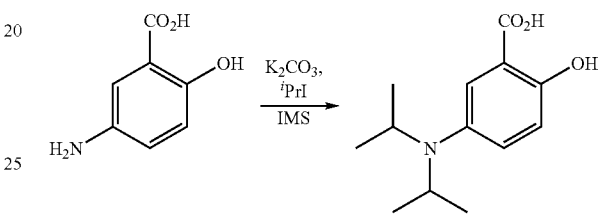

A mixture of 5-aminosalicylic acid (3.3 g, 21.6 mmol), 2-iodopropane (9.1 g, 53.9 mmol) and potassium carbonate (7.4 g, 54 mmol) was stirred at 50° C. in IMS (300 ml) and water (100 ml) for 4 days. Heating was stopped and the mixture concentrated to a solid, which was washed with 100 ml CH$_2$Cl$_2$. The washings were discarded and the solid heated in IMS (200 ml) for 30 minutes at 40° C. When heating was stopped, magnesium sulphate was added and stirring continued for 25 minutes. After filtration to remove the inorganic solids the solution was concentrated and purified by silica chromatography (eluent 10-20% methanol/CH$_2$Cl$_2$). This gave 0.5 µg of 4-diisopropylaminosalicylic acid.

$^1$H NMR (δ, 250 MHz, d6-DMSO): 1.51 (12H, brd, 5.75 Hz), 3.9-3.5 (1H, br), 4.41 (2H, br), 7.21 (1H, d, 8.8 Hz), 7.70 (1H, dd, 8.8, 2.7 Hz), 8.12 (1H, brs)

EXAMPLE 8

Study on the Effects of New Compounds According to the Invention on PPARγ Activation/Expression and Regulation of Cell Proliferation and Apoptosis Materials and Methods Compounds 5-ASA was purchased at Sigma-Aldrich™ (St Quentin Fallavier, France). Rosiglitazone was acquired at Spi Bio™ (Massy, France). The new molecules 13, 14, 17, 26, 31, 38 (FIG. 1A) were given by Giuliani SpA™ (Milano, Italy) and synthesized by SAFC Pharma™ (Manchester, England).

Cell Lines

The colon carcinoma cell line HT-29 STD (ATCC HTB-38) was routinely grown in DMEM supplemented with 10% heat-FCS, and antibiotics. Cells were grown in monolayers, incubated at 37° C. in 5% CO$_2$ and 95% relative humidity.

Transient Transfection with PPARγ and Stimulation of Cells

HT-29 STD cells were transiently transfected using the Effectene™ transfection reagent (Qiagen™) according to instructions from the manufacturer. To test PPARγ activation, we performed transfection with 500 ng of a minimal promoter construct containing two copies of PPRE obtained from the cytochrome p450 4A (2XCYP) (1). The renilla luciferase plasmid (0.1 g/well) was also transfected as an internal control for monitoring transfection efficiency and for normalizing the firefly luciferase activity. Transfected cells were left for 48 hours incubation at 37° C. Stimulations were performed after incubation of cells during 3-6-9-12-15-18-24 hours with the compounds 13, 14, 17, 26, 31, 38 at a concentration of 30 mM and compared with the two PPARγ synthetic ligands 5-ASA 30 mM (2) and rosiglitazone $10^{-5}$ M (2) used as positive controls. The pH of the drug solutions was adjusted to 7.4 with NaOH. Total cell extracts were prepared using the Passive Lysis Buffer (Promega™, Madison, Wis.). Luciferase activity was assayed in 20 μl of the extract using the Promega™ Dual Luciferase assay system according to the manufacturer's protocol. Transfections were assayed in triplicate in at least three separate experiments. The luciferase activity was expressed as fold of the activity obtained in cells treated with the different molecules divided by luciferase activity from non-stimulated cells.

Evaluation of PPARγ and β-Actin by Western Blot Analysis

The total proteins were obtained by cell homogenization in an extraction buffer consisting of PBS with 2% Triton™, Phenyl Methyl Sulphonyl Fluoride (PMSF) 100 mM and a classical protease inhibitor cocktail (2). The total proteins were then separated by polyacrylamide gel electrophoresis and electroblotted. Polyvinylidendifluoride (PVDF) membranes were incubated overnight with rabbit polyclonal primary antibody directed against PPARγ (dilution 1/500, TEBU, Le Perray en Yveline, France). β-actin was detected using a rabbit monoclonal primary antibody diluted at 1/10, 000 (Sigma). Immunodetection with a secondary peroxidase-conjugated antibody (1/1000, Dako™, Trappes, France) and chemiluminescence was performed according to the manufacturer's protocol (ECL™, Amersham Pharmacia Biotech™, Orsay, France). Optical density values of PPARγ were given for each condition in proportion to the quantity of the internal control β-actin in the same sample (2).

Analysis of Cell Proliferation by Ki-67 Immunostaining

After 24 h of culture, HT-29 STD cells were treated during 24 h with the new molecules 13, 14, 17, 26 and 31, at 30 mM. 5-ASA (30 mM) and rosiglitazone ($10^{-5}$M) were used as positive controls. The molecule 38 (example 7) was not included in this experiment due to its poor solubility. The pH of the drug solutions was adjusted to 7.4 with NaOH. Cells were fixed in PFA 4%, permeabilized in PBS containing 0.1% Triton X-100™ at 4° C. and then incubated with goat normal serum and blocking buffer (1% BSA in PBS) to minimize non-specific adsorption of the antibody.

Cell proliferation was assessed by a nuclear Ki-67 staining using mouse monoclonal primary antibody directed against Ki-67 (dilution 1:50 overnight; ZYMED™ Clinisciences™, Montrouge, France). Primary antibody was revealed with Alexa 594 donkey anti-mouse IgG conjugated to acridin red fluorochrome (dilution 1:100, Molecular Probes™, Invitrogen™, Cergy Pontoise, France). Nuclei were stained with Hoescht 33342 solution (0.125 mg/mL) (Sigma-Aldrich™) and visualized under a fluorescence microscope (Leica™, Bensheim, Germany). Negative controls consisted of staining with a non-specific mouse serum instead of the specific antibody. Counts of at least 500 cells/sample were systematically performed blindly in one experiment. The results were expressed as the mean±SEM of the number of stained cells.

Detection of Apoptosis

After 24 h of culture, HT-29 STD cells were treated during 24 h with the new molecules 13, 14, 17, 26 and 31, at a concentration of 30 mM. 5-ASA (30 mM) and rosiglitazone ($10^{-5}$M) were used as positive controls. The molecules 17 and 38 (examples 3, 7) were not included in this experiment due to their poor solubility. The pH of the drug solutions was adjusted to 7.4 with NaOH. Cells undergoing apoptosis were identified by enzymatic labelling of DNA strands using a terminal transferase dUTP nick end labelling assay (TUNEL assay, Roche Diagnostics™, Meylan, France). Counts of at least 500 cells/sample were systematically performed blindly in one experiment. The results were expressed as the mean±SEM of the number of stained cells.

Results

It has been observed that the new molecules 17 (example 3) and 31 (example 6) induce PPARγ activation. Compound 26 (example 4) also induces PPARγ, but to a lesser extent. Activation of PPARγ results in a cascade of reactions leading to a binding to specific DNA sequence elements termed peroxisome proliferator response elements (PPRE) (7-9).

We investigated PPARγ transcriptional activity by transient transfections of epithelial cells with the renilla luciferase PPRE plasmids. Cells were stimulated with the different molecules during 24 hours. Analysis of PPARγ activity in transfected HT-29 cells showed that the new molecules 17 (example 3) and 31 (example 6) at a concentration of 30 mM increased the reporter gene activity by two-fold thereby displaying an activity similar to 5-ASA and rosiglitazone (FIG. 1B). Molecules 13, 14 and 38 (examples 1, 2, 7) at a concentration of 30 mM exerted a rapid cytotoxic effect on epithelial cells limiting the investigation of PPARγ activation after 6 hours (FIG. 1B).

The new molecules 17, 26 and 31 induce PPARγ expression. The capacity of new molecules to induce PPARγ expression at the protein levels in the HT-29 cell line. A mean 2-fold induction of PPARγ protein levels quantified by western blot was observed in cells treated during 24 hours with the molecules 17, 26 and 31 (FIG. 2).

Figure 3:
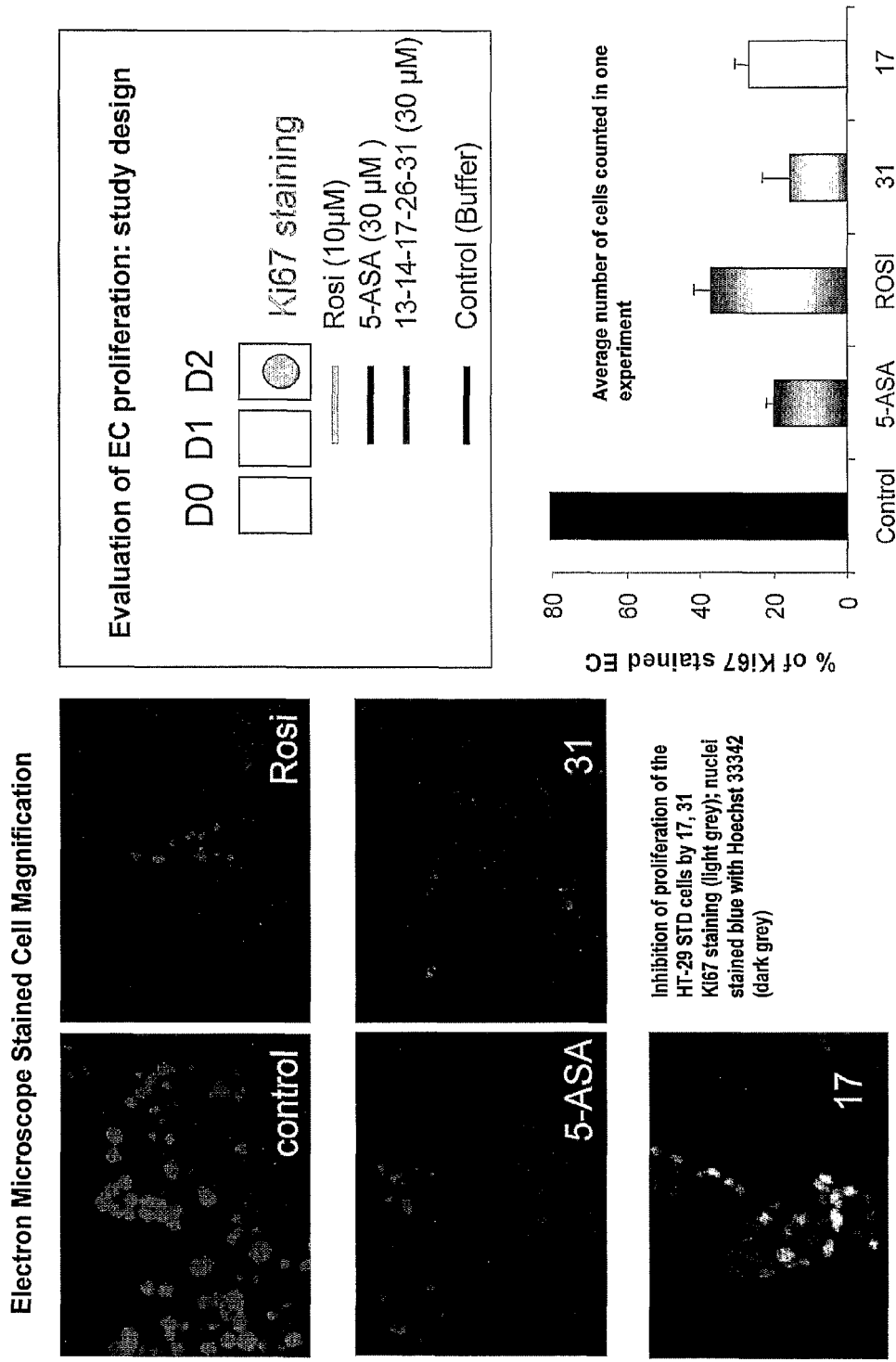

The new molecules 17 and 31 (examples 3 and 6) inhibit epithelial cell proliferation. We evaluated in HT-29 STD cell line the role of the new molecules in the regulation of cell proliferation (FIG. 3). Cell proliferation was assessed by nuclear protein Ki-67 staining expressed in proliferating cells, the presence of Ki-67 being necessary to maintain cell proliferation (10). Compared to untreated cells, incubation of HT-29 cells for 24 h with the molecules 17 and 31 (30 mM) resulted in a 67 to 75% inhibition of cell proliferation (FIG. 3). The cell proliferation effects of compound 26 were not tested, since it has a lesser effect as a PPAR-gamma activator.

Similar results were obtained with the two positive controls rosiglitazone ($10^{-5}$M) and 5-ASA (30 mM) used at their optimal concentrations. Demonstration of the potential antimitogenic effect of the molecules 13, 14 and 26 (examples 1, 2, 4) was limited by their rapid cytotoxic effects on epithelial cells at this concentration (data not shown).

Figure 4:
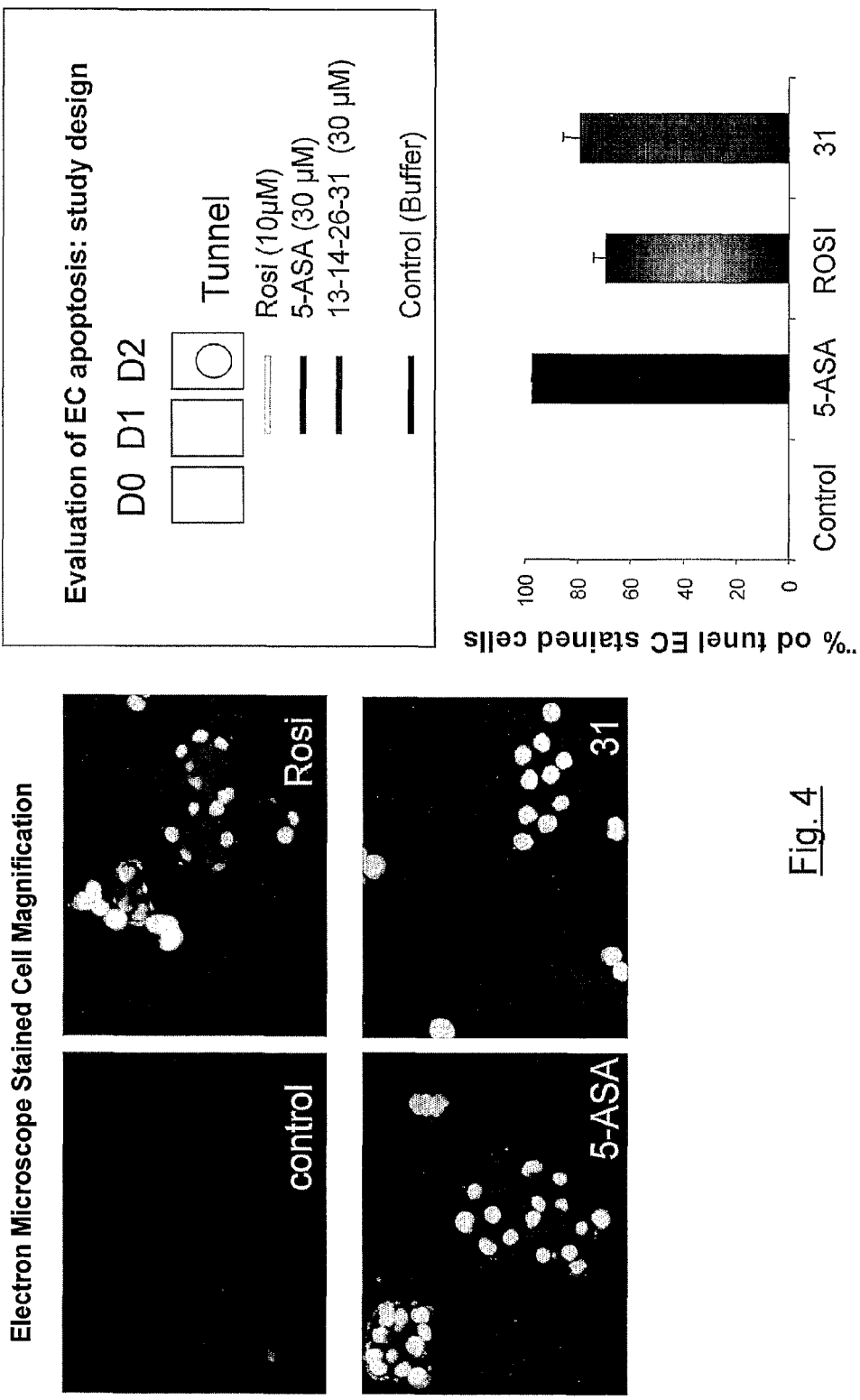

The new molecule 31 (example 6) induces epithelial cell apoptosis through PPARγ. Similarly to rosiglitazone and 5-ASA, the molecule 31 displayed apoptosis in 80% of epithelial cells identified by labelling DNA strand breaks using a terminal transferase dUTP nick end labelling (TUNEL) (FIG. 4). Similarly to the previous experiment, molecules 13, 14 and 26 induced a rapid cytotoxic effect at 30 mM impeding cell apoptosis analysis.

EXAMPLE 9

Study on the Effects of New Compounds on PPARγ Activation

Materials and Methods

Compounds

5-ASA was purchased at Sigma-Aldrich™ (St Quentin Fallavier, France). The new molecules 13, 14, 17, 26, 28, 31, 38 (FIG. 1A) were synthesized as described in examples 1-7.

Cell Lines

The colon carcinoma cell line HT-29 STD (ATCC HTB-38) was routinely grown in DMEM supplemented with 10% heat-FCS, and antibiotics. Cells were grown in monolayers, incubated at 37° C. in 5% $CO_2$ and 95% relative humidity.

Transient Transfection with PPARγ and Stimulation of Cells

HT-29 STD cells were transiently transfected using the Effectene™ transfection reagent (Qiagen™) according to instructions from the manufacturer. To test PPARγ activation, we performed transfection with 500 ng of a minimal promoter construct containing two copies of PPRE obtained from the cytochrome p450 4A (2XCYP) (1). The renilla luciferase plasmid (0.1 µg/well) was also transfected as an internal control for monitoring transfection efficiency and for normalizing the firefly luciferase activity. Transfected cells were left for 24-hours incubation at 37° C. Stimulations were performed after incubation of cells during 18 hours with the compounds 13, 14, 17, 26, 28, 31 and 38 (see FIG. 6) at a concentration of 1 mM and compared with the two PPARγ synthetic ligands 5-ASA 30 mM (2) used as positive controls. The pH of the drug solutions was adjusted to 7.4 with NaOH. Total cell extracts were prepared using the Passive Lysis Buffer (Promega™, Madison, Wis.). Luciferase activity was assayed in 20 µl of the extract using the Promega™ Dual Luciferase assay system according to the manufacturer's protocol. Transfections were assayed in triplicate in at least three separate experiments. The luciferase activity was expressed as fold of the activity obtained in cells treated with the different molecules divided by luciferase activity from non-stimulated cells.

Results

Activation of PPARγ results in a cascade of reactions leading to a binding to specific DNA sequence elements termed peroxisome proliferator response elements (PPRE) (7-9).

We investigated PPARγ transcriptional activity by transient transfections of epithelial cells with the renilla luciferase PPRE plasmids. To evaluate if the new molecules have more efficacy than 5-ASA to stimulate PPAPγ activation, we tested these molecules at a concentration of 1 mM. The effect of the new molecules at a concentration of 1 mM was compared to 5-ASA, used as a positive control at optimal concentration of 30 mM. Cells were stimulated with the different molecules during 24 hours. Analysis of PPARγ activity in transfected HT-29 cells showed that the new molecules increased the reporter gene activity thereby displaying an activity similar or superior to 5-ASA (concentration of the new molecules was 30 times less, see FIG. 6).

EXAMPLE 10

Study on the Effect of the Compounds on Colon Cancer Cell Growth

The following substances 13, 14, 17, 26, 28, 31 and 38 were tested for their ability to modulate colon cancer cell growth. No experiment was performed with the compound 28 as this substance was not soluble in the culture medium.

For this purpose, three human colon carcinoma cell lines (i.e. HT-29, HT-115 and DLD-1) were used. These cell types were selected on the basis of the cyclooxigenase-2 (COX-2) expression. Indeed, HT-115 cells express a biologically active COX-2, HT-29 cells express a non-functional COX-2 isoform, and DLD-1 are COX-2-deficient cells.

HT-29 and DLD-1 cells were cultured in McCoy and RPMI1640 media respectively, supplemented with 10% fetal bovine serum (FBS), 1% penicillin/streptomycin (P/S) and 50 µg/ml gentamycin. HT-115 were cultured in DMEM medium supplemented with 15% FBS and 1% P/S. Cells were maintained in a humidified incubator at 37° C., in the presence of 5% $CO_2$.

For cell growth assays, single-cell suspensions were plated at $2 \times 10^3$ cells/well ($4 \times 10^3$ cells/well for HT115) in 96-well culture dishes in medium containing 0.5% FBS and allowed to adhere. The non-adherent cells were then removed, and fresh medium containing 0.5% FBS was added into each well. Cells were cultured in the presence or absence of the specified substances. Each substance was dissolved as a 25 mM stock solution in culture medium containing 0.5% FBS, and the pH of each stock solution was adjusted to 7.4, if necessary, with NaOH. Substances were used at a final concentration ranging from 0.5 to 10 mM. Cell proliferation was determined by measuring the incorporation of 5-bromo-2'-deoxyuridine (BrdU) into DNA using a commercially available cell proliferation kit (Roche Diagnostics™, Monza, Italy). BrdU was added to the cell cultures during the last 6 hours of incubation, and the level of BrdU-positive cells was assessed after 48 h culture by enzyme-linked immunosorbent assay (ELISA).

Optical density (OD) was determined at 450 nm using an ELISA reader. Experiments were performed in triplicate and the results are reported as the mean±standard deviation (SD).

To assess further the effect of the compound 14 on colon epithelial cell growth, serum-starved DLD-1 cells were incubated in 0.2 µM carboxyfluorescein diacetate succinimidyl ester (CFSE) (Invitrogen™, Milan Italy) at 37° C. for 30 minutes, then extensively washed and cultured with or without the addition of the compound. After 2 days culture, CFSE fluorescence was evaluated and the proportion of cells undergoing divisions was determined, thus allowing calculation of both precursor frequency and proliferative index.

The effect of the compound 14 on colon epithelial cell death was also assessed. To this end, cells were cultured as indicated above for 2 days and then the fraction of Annexin V (AV) and/or propidium iodide (PI)-positive cells was evaluated using a commercially available kit (Beckmann Coulter™, Milan, Italy). To evaluate whether the effect of the compound 14 on colon epithelial cell death was dependent on caspase activity, cells were pre-incubated with z-VAD-fmk (40 µM), a pan-caspase inhibitor, for 1 hour prior to adding the compound 14 (1.5 mM). The fraction of AV and PI-positive cells was determined after 48 hours culture as indicated above.

Results

The compounds differed in their ability to inhibit colon cancer cell growth. Results are shown in FIGS. 7 and 8. Table shows the percentage of inhibition of growth of DLD-1 cells by the specified compounds. The substances 13, 14, 17, 26, and 38 exhibit a marked anti-proliferative effect. Among these substances, the compounds 13 and 14 significantly reduced the cell growth, in a dose-dependent fashion, in each of the three cell lines tested (FIGS. 7A and 7B). More than 90% of cell growth inhibition was seen when compounds were used at a final concentration of 10 mM. The anti-mitogenic effect of the compounds 17, 26 and 38 was observed only at concentrations of 2.5 mM or higher (FIG. 8A, 8C, 7D).

The compound 31 significantly inhibited cell growth when used at high doses (10 mM) (FIG. 7C).

Overall the above data indicate that substances 13, 14, and 38 are the most powerful suppressors of colon cancer cell growth. However, precipitates developed in cell cultures carried out in the presence of the substances 13 and 38. This was followed by a massive cell death, which makes it difficult to judge if the anti-proliferative effect of these compounds was due to either their anti-mitogenic action or toxic effect. Based upon these findings, subsequent experiments focused on the use of the compound 14.

First, the inhibitory effect of the compound 14 on the growth of DLD-1 cells was confirmed by flow-cytometry. To track cell proliferation, cells were labeled with CFSE. In line with the BrdU assay data, the compound 14 inhibited the proliferation of DLD-1 cells (FIG. 9). Importantly, after 48 hour treatment, the fraction of proliferating cells decreased from 90±4% in untreated cultures to 48±7, 21±11 and 11±6% in cell cultures treated with 0.5, 1 and 2.5 mM.

To examine whether the compound 14 also regulated the survival of colon cancer cells, DLD-1 cells were cultured in the presence or absence of such a compound for 48-hours and then the percentage of Annexin V and/or PI-positive cells was evaluated by flow cytometry. As shown in FIG. 10A, compound 14 significantly enhanced the fraction of cell death when used at a final concentration of 1.5 or 3 mM. To explore the involvement of caspases in the 14-mediated DLD-1 cell death, cells were preincubated with a pan-caspase inhibitor, Z-VAD, and then treated with 14. As shown in the representative experiment in FIG. 10B, treatment of cells with Z-VAD largely reduced the percentage of AV/PI-positive cells.

The percentage of DLD-1 cell inhibition by graded doses (0.5-10 mM) of the specified compounds is present in Table 1. Cells were cultured in the presence or absence of the compounds, and cell growth was then assessed by the colorimetric (BrdU) assay after 48-hours culture.

EXAMPLE 11

Molecular Modelling

Molecular modelling studies were performed using SYBYL software version 6.9.1 (Tripos Associates Inc™, St Louis, Mo.) running on Silicon Graphics™ workstations. Three-dimensional model of the zwitterions form of 5-ASA was built from a standard fragments library, and its geometry was subsequently optimized using the Tripos force field (3). As the $pK_a$ of compounds is still unknown, the SPARC online calculator was used to determine the species occurring at physiological pH (7.4) (http://ibmlc2.chem.uga.edu/sparc/index.cfm). Three-dimensional models of ionized compounds were built from a standard fragments library, and their geometry was subsequently optimized using the Tripos force field (3) including the electrostatic term calculated from Gasteiger and Huckel atomic charges. The method of Powell available in Maximin2 procedure was used for energy minimization until the gradient value was smaller than 0.001 kcal/mol.Å. The structure of the human PPARγ ligand-binding domain was obtained from its complexed X-Ray crystal structure with the tesaglitazar (AZ 242) available in the RCSB Protein Data Bank (1I7I) (4,5). Flexible docking of the compounds into the receptor active site was performed using GOLD software (6). The most stable docking models were selected according to the best scored conformation predicted by the GoldScore (6) and X-Score scoring functions (7). The complexes were energy-minimized using the Powell method available in Maximin2 procedure with the Tripos force field and a dielectric constant of 4.0 until the gradient value reached 0.01 kcal/mol.Å. The anneal function was used defining the ligand a hot region (10 Å).

Docking Studies

All new molecules fit tightly with the PPARγ-LBD interacting via hydrogen bonding with His-323, His-449, Tyr-473 and Ser-289 considered as key determinants required for molecular recognition and PPARγ activation (11-12) (FIG. 5A, 5C, 5D). Docking for 5-ASA is shown in FIG. 5B.

CONCLUSIONS

It has previously shown that anti-inflammatory effects of 5-ASA were mediated through PPARγ mainly expressed in the colon by epithelial cells (2). The rational development of the first 6 new optimized 5-ASA molecules based on docking analysis revealed that the 2 molecules 31 and 17, used at a concentration of 30 mM, activate PPARγ and induce its expression by intestinal epithelial cells. These 2 new molecules also inhibit epithelial cell proliferation and induce apoptosis, two important mechanisms involved in the development of colonic cancer and attributed to PPARγ activation. Concerning the 4 other molecules (13, 14, 26, 38), most of them have direct cytotoxic effects on epithelial cells at a concentration of 30 mM, impeding the analysis of PPARγ activation and regulation and evaluation of cell proliferation and apoptosis.

This first set of examples of the invention (Example 8) shows the ability of two optimized molecules 31 and 17 to stimulate PPARγ expression and activation and to regulate epithelial cell proliferation and apoptosis. The cytotoxic effects on epithelial cells of compounds 13, 14 and 26 at 30 mM may be related to the presence in their structure of a highly reactive hydroxamic acid group known to display a great affinity for many various enzymes.

The second set of examples of the invention (Example 9) indicates that also the other test the molecules display an activity similar to, or superior to 5-ASA at a working concentration thirty times less than that of 5-ASA, over a period of 24 hours.

The final set of examples of the invention (Example 10) shows that the compounds affect the inhibition of the growth of the colon cancer cell lines, HT-29, HT-115 and DLD1 to varying degrees, with compounds 13, 14 and 38 showing the highest effects. In order to clarify the nature of the cell death, compound 14 was further investigated and was confirmed, by flow-cytometry, to inhibit the growth of DLD-1 colon cancer cells with increasing concentration over time.

These molecules are also active on cells that do not express COX-2, and thus the molecules of the present invention may be used in cells which do not express COX-2 for the purposes of treating tumours and other applications as herein described.

OVERALL CONCLUSIONS

The synthesized highest ranking compounds, indicated from modelling studies, all show an activity similar/superior to that of mesalazine.

REFERENCES

1. Dubuquoy, L., E. A. Jansson, S. Deeb, S. Rakotobe, M. Karoui, J. F. Colombel, J. Auwerx, S. Pettersson, and P. Desreumaux. 2003. Impaired expression of peroxisome proliferator-activated receptor gamma in ulcerative colitis. *Gastroenterology* 124:1265-1276.
2. Rousseaux C, Lefebvre B, Dubuquoy L, Lefebvre P, Romano O, Auwerx J, Metzger D, Wahli W, Desvergne B, Naccari G C, Chavatte P, Farce A, Bulois P, Cortot A, Colombel J F, Desreumaux P. Intestinal anti-inflammatory effect of 5-amino salicylic acid is dependent on PPARγ. *J Exp Med* 2005; 201: 1205-15.
3. Clark, M. C. R. D. I. V. O., N. 1989. Validation of the General Purpose Tripos 5.2 Field. *J. Comput Chem.* 10:982-1012.
4. Gampe, R. T., Jr., V. G. Montana, M. H. Lambert, A. B. Miller, R. K. Bledsoe, M. V. Milburn, S. A. Kliewer, T. M. Willson, and H. E. Xu. 2000. Asymmetry in the PPAR-gamma/RXRalpha crystal structure reveals the molecular basis of heterodimerization among nuclear receptors. *Mol Cell* 5:545-555.

5. Jones, G., P. Willett, R. C. Glen, A. R. Leach, and R. Taylor. 1997. Development and validation of a genetic algorithm for flexible docking. *J Mol Biol* 267:727-748.
6. Wang, R., L. Lai, and S. Wang. 2002. Further development and validation of empirical scoring functions for structure-based binding affinity prediction. *J Comput Aided Mol Des* 16:11-26.
7. Westin, S., R. Kurokawa, R. T. Nolte, G. B. Wisely, E. M. McInerney, D. W. Rose, M. V. Milburn, M. G. Rosenfeld, and C. K. Glass. 1998. Interactions controlling the assembly of nuclear-receptor heterodimers and co-activators. *Nature* 395:199-202.
8. Mangelsdorf, D. J., C. Thummel, M. Beato, P. Herrlich, G. Schutz, K. Umesono, B. Blumberg, P. Kastner, M. Mark, P. Chambon, and et al. 1995. The nuclear receptor superfamily: the second decade. *Cell* 83:835-839.
9. Misra, P., E. D. Owuor, W. Li, S. Yu, C. Qi, K. Meyer, Y. J. Zhu, M. S. Rao, A. N. Kong, and J. K. Reddy. 2002. Phosphorylation of transcriptional coactivator peroxisome proliferator-activated receptor (PPAR)-binding protein (PBP). Stimulation of transcriptional regulation by mitogen-activated protein kinase. *J Biol Chem* 277:48745-48754. Epub 42002 September 48727.
10. Gerdes, J. et al. 1986. Growth fractions in breast cancers determined in situ with monoclonal antibody Ki-67. *J Clin Pathol* 39, 977-80.
11. Nolte, R. T., G. B. Wisely, S. Westin, J. E. Cobb, M. H. Lambert, R. Kurokawa, M. G. Rosenfeld, T. M. Willson, C. K. Glass, and M. V. Milburn. 1998. Ligand binding and co-activator assembly of the peroxisome proliferator-activated receptor-gamma. *Nature* 395:137-14
12. Xu, H. E., M. H. Lambert, V. G. Montana, K. D. Plunket, L. B. Moore, J. L. Collins, J. A. Oplinger, S. A. Kliewer, R. T. Gampe, Jr., D. D. McKee, J. T. Moore, and T. M. Willson. 2001. Structural determinants of ligand binding selectivity between the peroxisome proliferator-activated receptors. *Proc Natl Acad Sci USA* 98:13919-13924. Epub 12001 November 13916.

TABLE 1

1% DLD-1 cell inhibition by graded doses (0.5-10 mM) of the specified compounds

| | % of growth inhibition | | | | |
|---|---|---|---|---|---|
| mM | 0.5 | 1 | 2.5 | 5 | 10 |
| 13 | 21.1 | 73 | 92.7 | 96.3 | 96.4 |
| 14 | 22.8 | 36 | 76.5 | 90.5 | 94.1 |
| 17 | 0 | 0 | 33.3 | 89.3 | 90.7 |
| 26 | 13.6 | 19 | 62 | 86 | 94.5 |
| 28 | | | NOT SOLUBLE | | |
| 31 | 0 | 0 | 0 | 8.8 | 31.7 |
| 38 | 6 | 11.1 | 51.9 | 85.9 | 94.5 |

The invention claimed is:

1. A compound of the general formula (I)

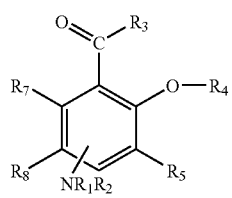

(I)

in which $R_1$ and $R_2$, which may be identical or different, are selected from the group consisting of —H, a linear or branched alkyl group having from 1 to 6 carbon atoms, or together form an aliphatic ring;

$R_3$ is selected from, —NHOH, —OH, —$OR_6$ in which $R_6$ is a linear or branched alkyl group having from 1 to 6 carbon atoms;

$R_7$, $R_8$ are hydrogen atoms; and $R_4$ and $R_5$, together form an aliphatic ring, fused to the benzene, with 1 to 2 heteroatoms selected independently from N or O; and salts thereof.

2. A compound as claimed in claim 1 wherein $R_1$ and $R_2$ are each independently selected from the group consisting of: —$CH_3$, —$C_2H_5$, isopropyl or propyl.

3. A compound as claimed in claim 1 wherein $R_4$ and $R_5$ form a ring according to the following formula (III)

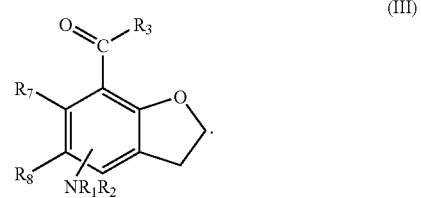

(III)

4. A compound selected from the group consisting of:
4-amino-N-hydroxy-2-methoxybenzamide,
5-amino-N-hydroxy-2-methoxybenzamide,
5-amino-2,3-dihydrobenzofuran-7-carboxylic acid,
5-amino-2-ethoxy-N-hydroxybenzamide,
5-amino-2-isopropoxybenzoic acid,
and
5-diisopropylaminosalicylic acid.

5. A compound according to claim 1 wherein $R_1$ and $R_2$, are both —$CH(CH_3)_2$.

6. A compound the represented by the following structure:

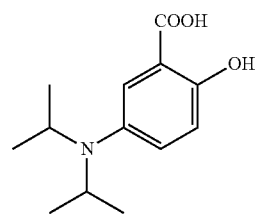

and salts thereof.

7. A compound according to claim 1 wherein $R_1$ and $R_2$, are both —H.

8. A compound according to claim 1 represented by the following structure

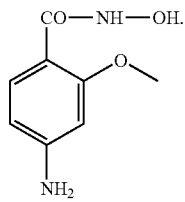

9. A compound represented by the following structure

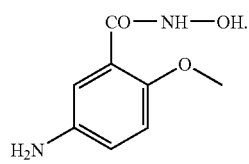

10. A compound represented by the following structure

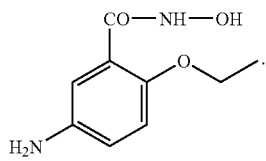

11. A compound represented by the following structure

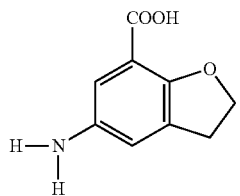

and salts thereof.

12. A compound represented by the following structure

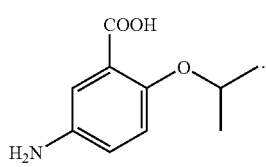

13. A pharmaceutical composition comprising one or more compounds as defined in claim 1 as active principles in combination with one or more pharmaceutically acceptable excipients or adjuvants.

14. A method of or treating colon tumours expressing the PPARγ receptors and the EGF receptors in a human or animal in need thereof, comprising administering to the human or animal a compound according to claim 1.

15. A method of treating Crohn's disease or ulcerative rectocolitis in a human or animal in need thereof, comprising administering to the human or animal a compound according to claim 1.

16. A method of treating Crohn's disease, ulcerative rectocolitis or colon cancer in a human or animal in need thereof, comprising administering to the human or animal a compound selected from the group consisting of 4-amino-N-hydroxy-2-methoxybenzamide, 5-amino-N-hydroxy-2-methoxybenzamide, 5-amino-2,3-dihydrobenzofuran-7-carboxylic acid, 5-amino-2-ethoxy-N-hydroxybenzamide, 6-amino-2,2-dimethyl-4H-benzo[1,3]dioxin-4-one, and salts thereof.

17. A compound represented by (I):

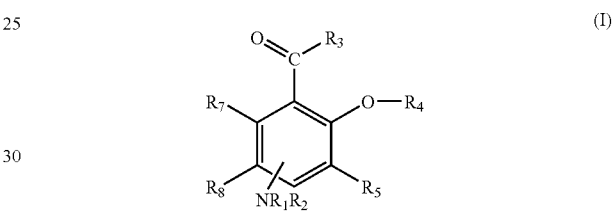

wherein:
$R_1$ and $R_2$, are each independently a linear or branched alkyl group having from 1 to 6 carbon atoms;
$R_3$ is —NHOH;
$R_4$ is a linear or branched alkyl group having from 1 to 6 carbon atoms, phenyl, or benzyl; and
$R_5$, $R_7$, $R_8$ are hydrogen atoms; and salts thereof.

18. The compound of claim 17 wherein $R_4$ is selected from the group consisting of —$CH_3$, —$CH_2CH_3$ and —$CH(CH_3)_2$.

* * * * *